(12) United States Patent
Kuduvalli

(10) Patent No.: US 7,505,559 B2
(45) Date of Patent: Mar. 17, 2009

(54) DETERMINING A TARGET-TO-SURFACE DISTANCE AND USING IT FOR REAL TIME ABSORBED DOSE CALCULATION AND COMPENSATION

(75) Inventor: Gopinath R. Kuduvalli, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 162 days.

(21) Appl. No.: 11/510,062

(22) Filed: Aug. 25, 2006

(65) Prior Publication Data

US 2008/0049896 A1    Feb. 28, 2008

(51) Int. Cl.
*A61N 5/10* (2006.01)
(52) U.S. Cl. .................................. 378/65; 378/205
(58) Field of Classification Search ............. 378/64–69, 378/205
See application file for complete search history.

(56) References Cited

U.S. PATENT DOCUMENTS

| | | | | |
|---|---|---|---|---|
| 5,037,374 | A | * | 8/1991 | Carol ............................ 600/1 |
| 6,501,981 | B1 | * | 12/2002 | Schweikard et al. ......... 600/427 |
| 6,540,756 | B1 | | 4/2003 | Vaughan |
| 6,889,695 | B2 | | 5/2005 | Pankratov et al. |
| 2006/0285641 | A1 | * | 12/2006 | Scherch ........................ 378/65 |

OTHER PUBLICATIONS

E. Coste-Maniere, D. Olender, W. Kilby, R.A. Schulz, "Robotic whole body stereotactic radiosurgery: clinical advantages of the CyberKnife® integrated system", The International Journal of Medical Robotics+Computer Assisted Surgery, www.roboticpublications. com, 2005 Robotic Publications Ltd.
"HI Art System", TomoTherapy™ Incorporated, Product Data Sheet, T-MKT-AP0033-1203, 4 pages, Jul. 2004.
Khan, Ph.D., Faiz M., "The Physics of Radiation Therapy", Third Edition, Lippincott Williams & Wilkins, 2003, title page, table of contents, and pp. 159-198.
"Tissue Inhomogeneity Corrections for Megavoltage Photon Beams", AAPM Report No. 85, Medical Physics Publishing, Aug. 2004, ISBN: 1-888340-47-9.
International Search Report, PCT/US07/18728 filed Aug. 23, 2007, mailed Nov. 17, 2008.

* cited by examiner

*Primary Examiner*—Hoon Song
(74) *Attorney, Agent, or Firm*—Blakely, Sokoloff, Taylor & Zafman, LLP

(57) ABSTRACT

An apparatus and method for determining a target-to-surface distance (TSD) between a target region in a body and an actual point of entry of a radiation beam into the body from a radiation source. The method may include determining an absorbed dose of radiation from the radiation beam at the target region using the TSD. The method may also include compensating for both the motion of the target region with respect to the radiation source, and the motion of surrounding tissue relative to the target region. The apparatus may include a sensor system to determine the actual point of entry of the radiation beam into the body.

52 Claims, 11 Drawing Sheets

DETERMINING A TARGET-TO-SURFACE DISTANCE AND USING IT FOR REAL TIME ABSORBED DOSE CALCULATION AND COMPENSATION

TECHNICAL FIELD

This invention relates to the field of radiation treatment and, in particular, to optimization of treatment delivery.

BACKGROUND

Pathological anatomies such as tumors and lesions can be treated with an invasive procedure, such as surgery, which can be harmful and full of risks for the patient. A non-invasive method to treat a pathological anatomy or other target is external beam radiation therapy. A "target" as discussed herein may be an anatomical feature(s) of a patient such as a pathological anatomy (e.g., tumor, lesion, vascular malformation, nerve disorder, etc.) or normal anatomy and may include one or more non-anatomical reference structures. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target region for therapeutic, rather than necrotic, purposes. For convenience, the term "radiation treatment" is used herein to include radiosurgery and/or radiotherapy unless otherwise noted.

Conventional radiation treatment can be divided into at least two distinct phases: treatment planning and treatment delivery. A treatment planning system may be employed to develop a treatment plan to deliver a requisite dose to a target region, while minimizing exposure to healthy tissue and avoiding sensitive critical structures. A target region may be a tumor. Alternatively, the target region may be another pathological anatomy. Surrounding tissue may be soft tissue or critical structures. Some examples of critical structures include vital organs, bones, and other physical structures that may be affected by radiation treatment. A treatment delivery system may be employed to deliver the radiation treatment according to the treatment plan. Treatment plans specify quantities such as the directions and intensities of the applied radiation beams, and the durations of the beam exposure. A treatment plan may be generated from input parameters such as beam positions, beam orientations, beam shapes, beam intensities, and radiation dose distributions (which are typically deemed appropriate by the radiologist in order to achieve a particular clinical goal). Sophisticated treatment plans may be developed using advanced modeling techniques and optimization algorithms. Treatment planning procedures, such as forward and inverse planning are conventionally known.

Some conventional radiation systems attempt to optimize the treatment plan prior to delivery. One such radiation system is the TomoTherapy Hi-Art System® available from TomoTherapy, Inc., of Madison, Wis. The Hi-Art System facilitates optimization of the treatment plan by calculating a planned dose into a phantom and then measuring a dose delivered into the phantom. Although such a system may facilitate optimization of the treatment plan during the treatment planning stage, it does not optimize radiation treatment based on the radiation actually absorbed at the target region during the treatment delivery stage.

Whether forward planning or inverse planning is used, conventional treatment plans assume specific treatment conditions. However, the actual treatment conditions during treatment delivery are typically different from the treatment planning assumptions. Such differences are not reflected in the treatment plan because they are unknown at the time of treatment planning and may result in an error between the planned radiation dose and the actual radiation dose. Conventional radiation treatment systems allow such deviations as acceptable tolerance errors and do not determine or generate any kind of record of the error. Furthermore, conventional radiation treatment systems do not allow the treatment delivery to be modified based on the difference between the planned dose and the actual dose delivered.

In particular, since it is seldom possible to measure dose distribution directly in patients treated with radiation, conventional radiation treatment systems derive model data on dose distributions from measurements in phantoms—tissue equivalent materials. The model data is used to predict dose distribution in an actual patient during treatment. For example, in one conventional radiation treatment system, the system can estimate the dose based on the accumulated depth, which is based on the tissue the radiation beam passes through. The model can use the actual depth and/or the accumulated depth (based on the tissue equivalent materials in the path of the radiation beam) to estimate the dose. However, it should be noted that the actual depth and accumulated depth used in treatment planning are assumed to be fixed values. The dose absorption may be estimated using the fixed values that are derived from a static CT image, which corresponds to a single instance in the breathing cycle of the patient. During treatment delivery the motion of the target and/or surrounding tissue may change the actual depth of the target region with respect to the surface of the body. Since the actual depth has been assumed during treatment planning to be fixed, motion that changes the actual depth during treatment planning may impact the actual dose absorbed at the treatment target. Conventional radiation treatment system do not take into account the internal movements of the target and the surrounding tissue with respect to one another and the surface of the body for determining the dose absorbed at the target region, but merely estimate the dose absorbed based on a fixed target depth.

BRIEF DESCRIPTION OF THE DRAWINGS

The present invention is illustrated by way of example, and not by way of limitation, in the figures of the accompanying drawings.

DETAILED DESCRIPTION

Figure 1A:
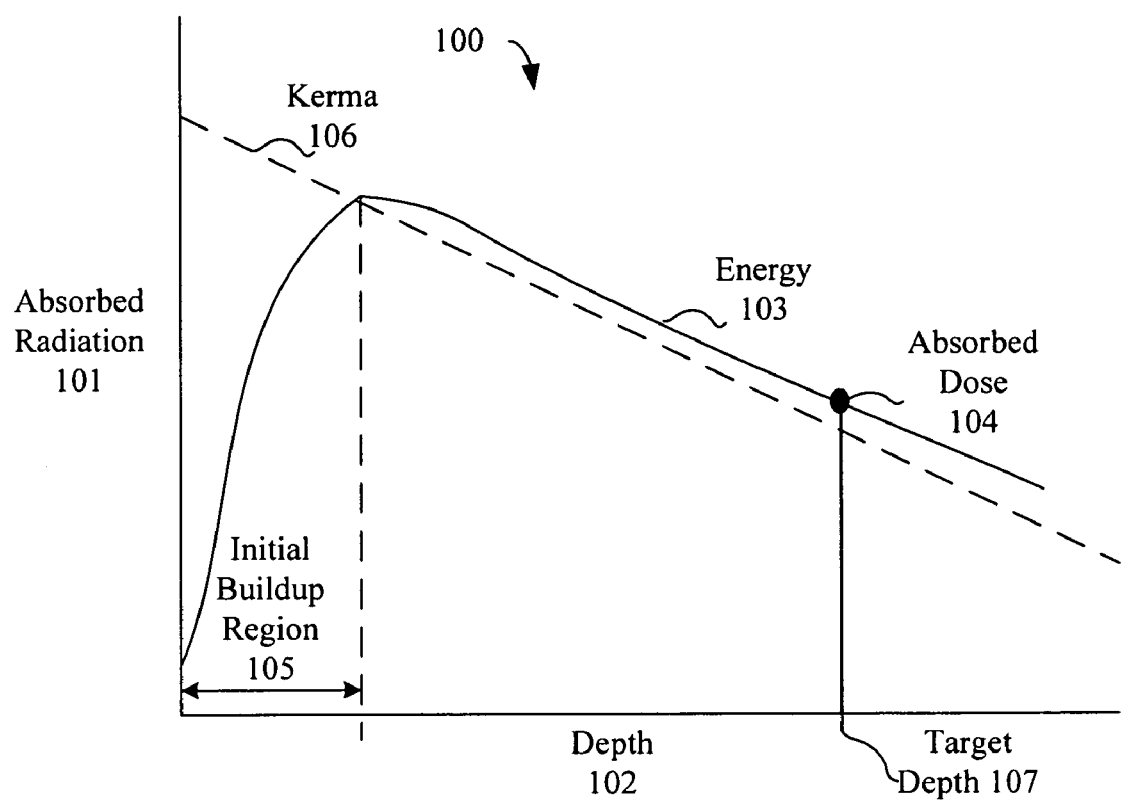
FIG. 1A illustrates a graph of one embodiment of the dose absorbed as a function of target depth and energy.

Embodiments of an apparatus and method for determining a target-to-surface distance (TSD) between a target region in a body and an actual point of entry of a radiation beam into the body from a radiation source are described. The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

The following description relates to a sensor system that determines the actual point of entry of the radiation beam into the body from the radiation source. In one embodiment, the sensor system may include a stereo-pair of optical video cameras and a laser. In another embodiment, the sensor system may include other devices for measuring the distance through the air to an object, such as sonar and radar devices. The measured position of the actual point of entry may be used, for example, to optimize radiation treatment delivery, to avoid collisions between the radiation source and the body, to measure the breathing cycle to compliment a motion tracking system, etc.

A method is described for delivering radiation beams to a target whose surrounding tissue is moving with respiration during treatment delivery such that the resulting radiation dose absorbed at the target is determined in real time. For example, the radiation dose absorbed at the target is determined during the current session of treatment or during a fraction of the session. This allows the system to compensate for motion of the surrounding tissue relative to the target so that the absorbed dose matches the planned dose of the treatment plan. The method may be performed using a stereo-pair of optical video cameras, which monitor the actual point of entry of the radiation beam into the body of the patient. Using the actual point of entry and the Source-to-Axis distance (SAD), the actual depth, which represents the depth of the penetration of the radiation beam before the radiation reaches the target region, can be computed during treatment delivery. Consequently, this target depth is used to compute the dose absorbed at the target region in real time.

A treatment plan is based on certain assumptions regarding the potential conditions during treatment delivery. However, the actual conditions during treatment delivery may be different from those assumptions. In particular, as described above, the actual depth of the target may change due to motion of the target region and intervening tissue movement during treatment. This movement, for example, may be caused by respiration of the patient.

In many medical applications, it is useful to accurately track the motion of a moving target region in the human anatomy. For example, in radiosurgery, it is useful to accurately locate and track the motion of a target region, due to respiratory and other patient motions during the treatment. Conventional methods and systems have been developed for performing tracking of a target treatment (e.g. radiosurgical treatment) on an internal target, while measuring and/or compensating for breathing and/or other motions of the patient. For example, U.S. Pat. Nos. 6,144,875 and 6,501,981, commonly owned by the assignee of the present application, describe such conventional systems. The SYNCHRONY® respiratory tracking system, manufactured by Accuray, Inc., can carry out the methods and systems described in the above patents. These conventional methods and systems correlate internal organ movement with respiration. However, these conventional technologies do not take into account internal movements of surrounding tissues relative to the target region. The motion of surrounding tissue of the target region may change the actual depth of the target region with respect to the surface of the body during treatment delivery. Given that the dose absorption is conventionally computed during treatment planning based on a static CT corresponding to a single instance in the breathing cycle, the combined effect is that the dose distribution during treatment delivery will differ from that computed during treatment planning. Described herein, however, is an apparatus that includes a motion tracking system to track and compensate for the motion of the target region with respect to the radiation source, and a sensor system that compensates for motion of surrounding tissue relative to the target region. For example, the motion tracking and sensor systems may be used in conjunction with a treatment delivery system to deliver radiation beams to a target region whose surrounding tissue is moving with respiration during treatment delivery such that the resulting radiation dose absorbed at the target region is determined in real time. This information can be used to ensure that the absorbed dose at the target region matches the planned dose accurately.

In one embodiment, the method described herein tracks the position of the tumor during treatment delivery and calculates an actual dose absorbed at the target region during treatment delivery, taking into account tumor and intervening tissue movement during treatment. During a treatment session, the radiation delivered in subsequent treatment positions may be adjusted to optimize the actual radiation delivered relative to the treatment plan. Such optimization may occur within a specified threshold. In certain embodiments, the optimization may be done during the current treatment, immediately following the current treatment, or during a subsequent fraction. In one embodiment, an operator may decide to augment the current treatment with additional treatment positions to optimize the treatment delivery so that the actual dose absorbed at the target region is closer to the calculated dose (e.g., planned dose) used to develop the treatment plan. In another embodiment, the operator may receive real-time feedback of these recommended dose adjustments during treatment and at the end of treatment.

Also described herein is a method for avoiding a collision of a housing of the radiation source and the body using the actual point of entry that is determined by the sensor system. Another method, described herein, includes measuring a breathing cycle of a patient's body using the actual point of entry. The breathing cycle measured by the sensor may also be correlated to the breathing cycle measured by the motion tracking system.

Absorbed dose in a patient varies with depth as the radiation beam is incident on a patient. The variation depends on many conditions, for example, beam energy, depth, field size, distance from source, beam collimation system, and the like. Dose calculations may include determining the depth dose variation along the central axis of the beam, using data such as percentage dose depth (PDD), tissue-air ratios, tissue-phantom ratios, tissue maximum ratio (TMR). These quantities may be derived from measurements made in phantoms using small ionization chambers (e.g., used with an ion chamber holder), or alternatively, other systems, for example, dosimetry systems such as TLD, diodes, and film. The ion chamber, for example, may be implemented with an ion chamber holder, also commonly known as Birdcage, which connects to the collimator receiver and holds a standard chamber (e.g., Farmer chamber) at a known distance (typically 80 cm) source-to-surface distance (SSD). Dose absorption can not be reduced to a simple equation, but empirical methods may be used to show that the absorbed dose at a point is a function of the target depth (e.g., TSD) and energy. This empirical data may be stored into files for retrieval by a system (e.g., look-up tables stored in memory). In another embodiment, the calculations may be performed on a processing system that has sufficient resources for computing, instead of using a look-up table.

FIG. 1A illustrates a graph 100 of one embodiment of the absorbed radiation 101 as a function of depth 102 of the target region and the energy of the radiation beam. The PDD increases with beam energy, as well as the absorbed radiation 101. Higher-energy beams have greater penetrating power and thus deliver a higher PDD. The PDD variation with depth 102 is governed approximately by exponential attenuation after the initial dose build-up. The initial buildup of dose becomes more and more pronounced as the energy is increased. In the case of lower energy x-rays, the dose builds up to a maximum value on or very close to the surface. But for higher-energy beams, the point of maximum dose lies deeper into the tissue or phantom. The region between the surface and the point of maximum dose is called the dose build-up region. For megavolt beams such as cobalt-60 and higher energies, the surface dose is much smaller than the maximum dose. This allows higher doses to be delivered to deep-seated tumors without exceeding the tolerance of the skin, since there is a higher PDD at the tumor (than with lower energy beams) and a lower dose at the skin surface. FIG. 1A, however, only illustrates how the absorbed radiation 101 changes with respect to the target depth for a single energy level, energy level 103. Energy level 103 increases in absorbed radiation 101 for the initial build-up region 105, at which point the absorbed radiation 101 starts attenuating. Using the data points on the graph, the absorbed radiation at certain depths may be determined. For example, when the target region 20 is at target depth 107 the amount of radiation absorbed at target region 20 is the absorbed dose 104. Data points that resemble graph 100 (for one or more energy levels) may be stored in a look-up table that may be retrieved by the treatment delivery system. Alternatively, the treatment delivery system may compute the data points of graph 100 during treatment delivery.

The physics of dose buildup may be explained as follows: (a) as the high-energy photon beam enters the patient or the phantom, high-speed electrons are ejected from the surface and the subsequent layers; (b) these electrons deposit their energy a significant distance away from their site of origin; (c) because of (a) and (b), the electron fluence and photon energy fluence continuously decrease with depth and, as a result, the production of electrons also decrease with depth. The net effect is that beyond a certain depth the dose eventually begins to decrease with depth.

Kerma 106 is the kinetic energy released in the medium. Kerma may be defined as the quotient of $dE_{tr}$ by dm, where $dE_{tr}$ is the sum of the initial kinetic energies of all the charged ionizing particles (electrons) liberated by uncharged ionizing particles (photons) in a material of mass dm, as represented in equation (1).

$$K = \frac{dEtr}{dm} \quad (1)$$

Because kerma represents the energy transferred from photons to directly ionizing electrons, the kerma is at its maximum at the surface and decreases with depth because of the decrease in the photon energy fluence. The absorbed radiation 101, on the other hand, first increases with depth as the high-speed electrons ejected at various depths travel downstream. As a result, there is an electronic build-up with depth. However, as the dose depends on the electron fluence, it reaches a maximum at a depth of approximately equal to the range of electrons in the medium. Beyond this depth, the dose decreases as kerma continues to decrease, resulting in a decrease in secondary electron production and hence a net decrease in electron fluence. The kerma curve is initially higher than the dose curve but falls below the dose curve beyond the build-up region. This effect is explained by the fact that the areas under the curves taken to infinity must be the same.

In one embodiment, a standard algorithm for dose calculations uses a ray-tracing function based on stored beam PDD data and off-axis ratios (OAR) data. PDD is the ratio of the absorbed dose at any depth to the absorbed dose at a fixed reference depth using a constant SSD. OAR is the ratio of absorbed dose at a given off-axis point to the dose at the central axis at the same depth. One way of characterizing the central axis dose distribution is to normalize dose at each depth with respect to a dose at a reference depth, as described with respect to FIG. 1B. TMR and OAR are both affected by target depth. The values for TMR and OAR may be physically measured for the specific beam characteristics of a radiation system and are dependent upon the energy spectrum of the beam. These values may be calculated using a phantom and may be stored in look-up tables of treatment delivery system, as described below.

Figure 1B:
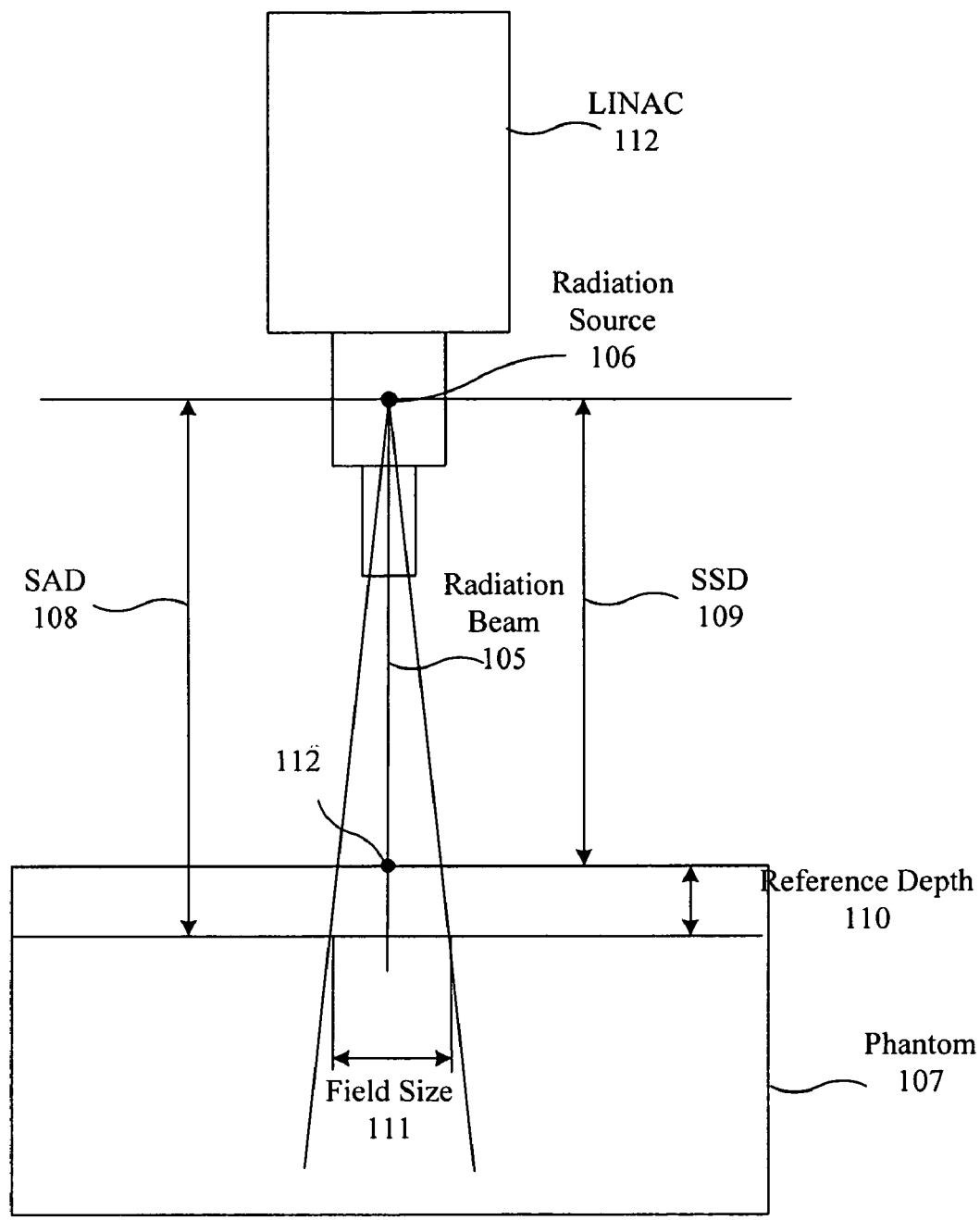
FIG. 1B illustrates a block diagram of one embodiment of a radiation beam delivered from a radiation source to a phantom.

FIG. 1B illustrates a block diagram of one embodiment of a radiation beam 105 delivered from a radiation source 106 to a phantom 107. Radiation source 106 is configured to direct radiation beam 105 towards the phantom 107. It should be noted that the radiation source as used herein may refer to the actual source of radiation, such as an x-ray target of a LINAC, or alternatively, the housing of the actual source of radiation, such as the housing of LINAC 112. In one embodiment, the radiation source 106 is an x-ray target of a linear accelerator (LINAC) 112 of a robot-based radiation system. Alternatively, the radiation source 106 may be a radiation source of a gantry-based radiation system or any another radiation system. The radiation beam 105 is incident on the phantom 107 at point of entry 112. The SSD 109 is the distance from the radiation source 106 to the surface of the phantom 107. The source-to-axis distance (SAD) 108 is the distance from the radiation source 106 to the isocenters or axis of rotation. In this embodiment, the SAD 108 is the distance between the radiation source 106 to a point in the phantom 107 that is at the target depth 110. It should be noted that this term has been used in describing the distance from the source to the axis of the gantry rotation of a gantry-based radiation treatment system. This axis of rotation is also known as an isocenters. In a robotic-based radiation treatment system, the SAD may be defined from the source to a point of convergence of radiation beams. This may be a single isocenters or multiple isocenters. Alternatively, the SAD may be defined as any point in or on the target region 20. Alternatively, the SAD 108 may be the distance between a collimator lens in a radiation source and the target region 20. For example, a robotic-based radiation treatment system, such as the CyberKnife® system developed by Accuray Inc., Sunnyvale, Calif., may direct radiation beams to a single isocenter, to multiple isocenters, or without any specific isocenters (i.e., the beams need only intersect with the pathological target volume and do not necessarily converge on a single point, or isocenter, within the target). In one embodiment, the SAD may be nominally 800 mm. Alternatively, other values of SAD may be used, such as 650 mm. The TPR is the ratio of absorbed dose at a given point to the dose at a fixed reference depth, reference depth 110, using a constant SSD 109. TPR data may be stored in a table, and may include factors measured for each collimator normalized at the reference depth, such as 15 mm. The range and resolution of depths can be anything, typically it is done from 0 to 300 mm in 1 mm steps, which, when needed, is obtained by internal software interpolation and extrapolation. The values for TPR may be difficult to measure directly. Accordingly, it may be easier to measure PDD and then covert to TPR. However, it may be beneficial to measure a few direct TPR measurements to verify the conversion from PDD to TPR. In one embodiment, the reference depth 110 is 15 mm. Alternatively, other reference depth values may be used. Field size 111 is the size of the radiation field. Usually, field size is defined at a reference SAD 108. Reference SAD 108 may be 800 mm, or alternatively, more or less than 800 mm. Field size 111 may be defined as the projection, on a plane perpendicular to the beam axis, of the distal end of the collimator as seen from the front center of the radiation source 106.

In one embodiment, the PDD values may be separated into two tables, an output factor (OP) that depends only on the collimator, and a tissue maximum ratio (TMR). The output factor is the ratio of absorbed dose of a particular field size to the dose at a reference field size. For example, the reference field size is 60 mm when the reference conditions are 15 mm for the reference depth and 800 mm for the SAD. The value for TMR is dependent on the field size and the depth of the point. Values may be linearly interpolated from calculated points for the PDD. The value for OAR depends on the field size, beam depth, and radial distance between the point of interest and the beam central axis. Values for the OAR may also be interpolated linearly, based on stored measurement points. Interpolations may be done based on perturbations of field size, depth and radial distanced from the central axis. The OAR measurements may also be stored in a table. The table may include OAR factors measured for the corresponding collimator normalized at the central axis at various depths. The measurements may be done at a fixed SDD of 800 mm, with varying depths. For example, four depths may be used, 15, 50, 100, and 200 mm. The range and resolution of radii can be any value as well, but typically it is done from 0 to 50 mm at 1 mm intervals. Internally, software may interpolate down to a resolution of 0.1 mm and extrapolates to 50 mm range, when needed. The number of stored beam data points, the number of beams, and the beam geometry may affect the amount of error associated with this dose calculation. Generally, more beams in a plan may yield smaller interpolation errors, because each beam's error should be random. The treatment delivery system, including the radiation source 106, may be configured to generate this data of these tables before treatment.

In general, the total dose absorbed to the target region is the sum of the combined dose resultant from each of the radiation treatment beams. In one embodiment, a dose calculation for a single radiation beam may be defined by the following equation, equation (2):

$$\text{dose}(x) = MU \times TMR(x) \times OP \times OCR(x) \times \left(\frac{800}{SAD(x)}\right)^2, \quad (2)$$

in which dose(x) is measured in cGy, a standard unit of radiation dose, and x is a point in space. The variable MU is the number of Monitor Units for the radiation beam. This is linearly related to the amount of time for which the radiation beam is active. The variable TMR(x) is the Tissue Maximum Ratio measured at the point (x). This models the attenuation of the beam due to passing through tissue. In one embodiment, the density values from the CT may be used to give an "effective depth" which determines the amount of attenuation. The variable OP is the Output Factor related to the collimator being used. In one embodiment, it is not spatially variant, but instead models the number of photons per unit time leaving the collimator. The variable OCR(x) is the Off-axis Correction Ratio, which models the radiation intensity in the cross section of the beam. The variable SAD(x) is the Source-Axis Distance. This is the distance from the radiation source to the point (x). This parameter models the inverse-square fall-off of photon count as distance from the radiation source increases. Although one equation is provided for performing a dose calculation, other delivery parameters and/or external factors may influence the dose calculation.

Where a total dose is tallied over time and multiple radiation beams, the total dose for multiple radiation beams may be defined by the following equation, equation (3):

$$D(x) = \sum_{i=1}^{N} w_i d_i(x), \quad (3)$$

in which D(x) is the total dose (measured in cGy), x is a point in space, i is a specific beam within a beam set, $\{B_i; 1<i<N\}$, where N may be any number (e.g., N=500), $w_i$ is a beam weight for the i-th beam, and $d_i(x)$ is the dose value absorbed to x when $w_i$ is set to unity.

Additional details of dose calculation are known in the art; accordingly, a more detailed description is not provided herein. More detailed descriptions of dose calculations may be referenced in, for example, Faiz M. Khan, *The Physics of Radiation Therapy*, 3d, Lippincott Williams & Wilkins 2003, and American Association of Physicists in Medicine, *AAPM Report No. 85: Tissue Inhomogeneity Corrections for Megavoltage Photon Beams*, Wisconsin, Medical Physics Publishing 2004.

In regard to the absorbed dose, the above dose calculation may be modified by changing the parameters in the equation above. For example, if the actual movement of the target region is known relative to the radiation beam at a given point in time, the dose may be recalculated using modified inputs for some or all of the variables of the dose calculation equation. In another example, the TSD between the target region and the surface of the body may be determined, and the dose may be recalculated using modified inputs for some or all of the variables of the dose calculation equation. As an illustrative example, if the position x changes to x+dx at time $t_0$. Then for all time $t>t_0$, the value OCR(x+dx) may be substituted for OCR(x) in the dose calculation equation. In other embodiments, other variables may be modified in addition to or instead of the off-axis correction ratio to calculate the actual radiation dose absorbed at the target region.

Figure 2:
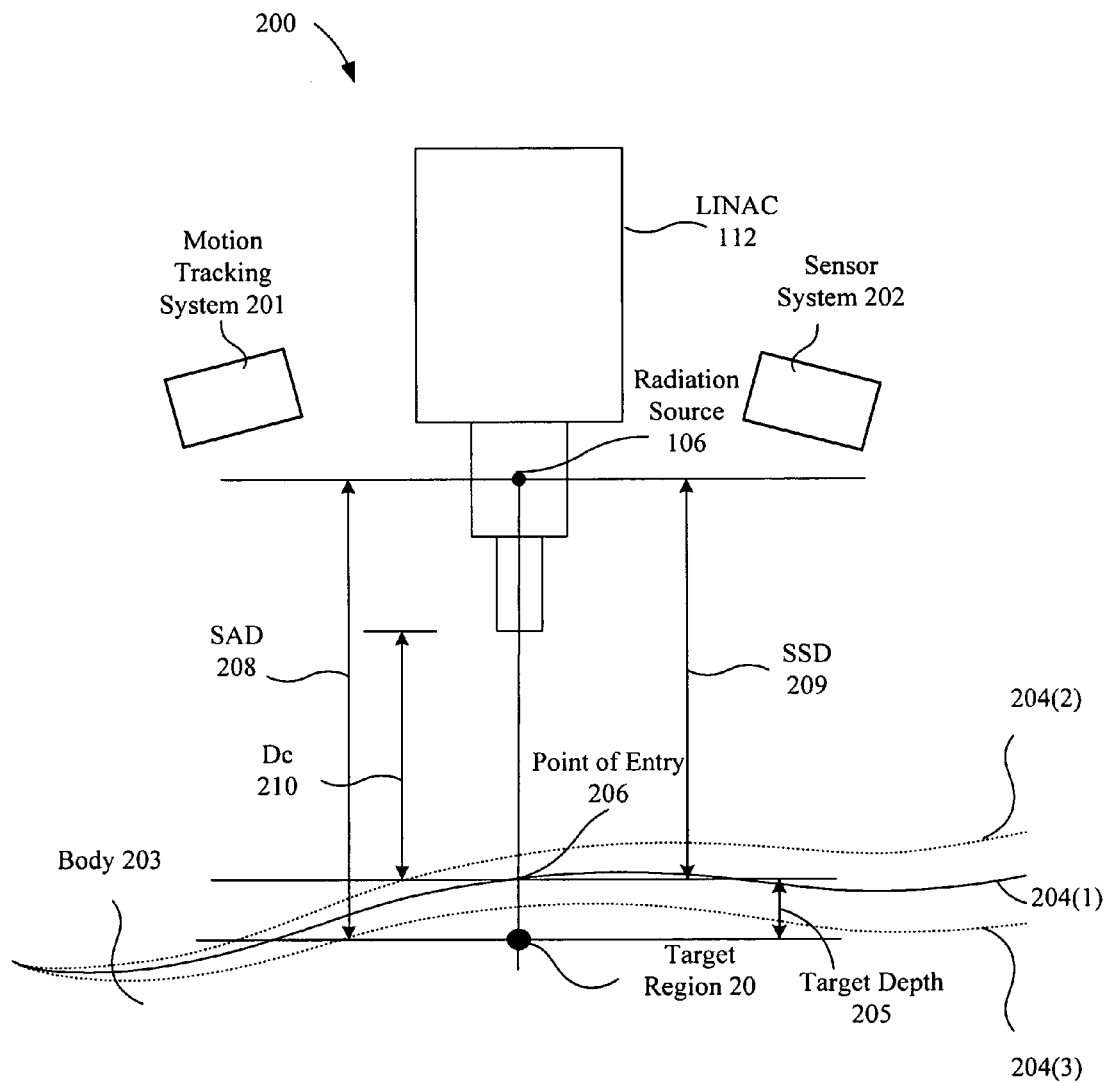
FIG. 2 illustrates a block diagram of one embodiment of a treatment delivery system including a motion tracking system for tracking motion of a target region and a point of entry sensor system for tracking motion of the surrounding tissue of the target region.

FIG. 2 illustrates a block diagram of one embodiment of a treatment delivery system 200 including a motion tracking system 201 for tracking motion of a target region 20 and a point of entry sensor system 202 for tracking motion of the surrounding tissue of the target region 20. The treatment delivery system 200 includes radiation source 106 of LINAC 112, motion tracking sensor 201, sensor system 202. Radiation source 106 directs radiation beam 105 at target region 20 of a body 203 of a patient. The patient may be a human, or even an animal. Body 203 moves during treatment, as illustrated by the surface 204 being in 3 positions, 204(1)-204(3). It should be noted that the three positions have been selected for ease of illustration and description, but the embodiments are not limited to three positions. Motion tracking system 201 is configured to locate and track the motion of target region 20 during treatment, due to respiration, for example. Motion tracking system 201 also is configured to compensate for the motion of the target region during treatment delivery. In compensating for the motion of the target region, motion tracking system 201 determines the SAD 208. In one embodiment, the LINAC 112, which includes the radiation source 106, may be moved to compensate for the motion of target region 20, as determined by motion tracking system 201. For example LINAC 112 may move to keep the SAD 208 fixed, based on the calculations made by the motion tracking system 201. Alternatively, the LINAC 112 is stationary, and the motion tracking system 201 determines a different value for SAD 208.

As described above, the motion tracking system 201 does not take into account internal movements of surrounding tissue relative to the target region. The motion tracking system 201 does not track movement of the surface or intervening tissue and/or organs with respect to the target region 20. As the surrounding tissue moves during treatment delivery, the actual depth 205 of the target region 20 may change with respect to the surface 204 of the body 203.

In order to compensate for changes in the actual depth 205 of the target region, sensor system 202 is configured to determine the actual point of entry 206 of the radiation beam 105. In one embodiment, the sensor system 202 may include a stereo-pair of optical video cameras and a laser (illustrated in FIG. 4). In another embodiment, the sensor system 202 includes a single camera and a laser to determine and monitor the actual point of entry 206. In another embodiment, the sensor system 202 includes only a pair of stereo cameras to determine and monitor the actual point of entry 206. Alternatively, the sensor system 202 may include other systems for measuring and monitoring the actual point of entry 206 to determine the distance through the air to the surface 204, such as sonar and radar devices. By determining and monitoring the point of entry 206, the SSD 209 can be determined. Sensor system 202 is mounted in a known location with respect to the radiation source 106, allowing the SSD 209 to be calculated upon determining the point of entry 206. Once the SSD 209 has been determined, the target depth 205 may be determined, since motion tracking system 201 has determined the SAD 208. For example, the SSD 209 may be subtracted from the SAD 208 to determine target depth 205. In another embodiment, the distance, Dc 210, between the housing of the LINAC 112 and the surface 204 of the body 203 may be determined. The distance between the radiation source 106 and the outer surface of the housing may be a known distance. Using this known distance and the SSD 209, the distance Dc 210 may be determined. In one embodiment, determining the distance Dc 210 may be used to avoid a collision of the housing of the radiation source 106 and the body 203.

In one embodiment, the target depth 205 may be used to determine the absorbed dose at the target region during treatment in real time. The absorbed dose and target depth 205 may be used by the treatment delivery system 200 to ensure that the absorbed dose at the target region 20 matches the planned dose of a treatment plan. This calculation may be performed for each beam, or alternatively, for a set of beams. For example, the absorbed dose may be determined for a single radiation beam using the target depth 205, and the treatment system 200 may modify the time that the radiation beam 105 is directed at the treatment target until the absorbed dose matches the planned dose in treatment planning for the single radiation beam. In another embodiment, the absorbed dose calculated for the single radiation beam may be stored and used to modify a subsequent radiation beam of the treatment plan, or a subsequent treatment plan.

In one exemplary embodiment, at treatment planning time, the absorbed dose at the target depth 205 is calculated and saved for each beam based on equation (2). For this, the planning system may use the target depth 205 calculated from a CT image and the corresponding values of TMR and OAR from the measured tables. The planning system may also model the target depth as a function of the breathing cycle, using two or more CT scans, or a 4D CT scan, acquired to cover the full breathing cycle. At treatment delivery, the target depth 205 is calculated in real time. Using the real time target depth and the values in TMR and OAR tables, the actual dose absorbed at the target is computed in real time, during treatment delivery. The absorbed MU is then adjusted in real time such that the dose is absorbed by the target is equal to the planned dose, calculated in the treatment plan. In one embodiment, the MU is adjusted in real time in the current radiation beam 105 at a current node until the absorbed dose matches the planned dose for that planned radiation beam. In another embodiment, no compensation for MU is done in real time during treatment, but the real time depth values available from the treatment delivery records are used to recalculate the absorbed dose using the treatment planning system. This recalculation can then be used to adjust the dose remaining fractions of current or subsequent treatment sessions. In another embodiment, no compensation for MU is done during the current beam, but the actual absorbed dose of the current beam may be used to adjust a subsequent beam of the current session. Alternatively, other method may be used to deliver the proper dose to the target region using the real time actual absorbed dose calculated using the determined target depth.

In another embodiment, the target depth 205 may be used to measure the patient breathing cycle. This breathing cycle may be correlated with the respiratory cycle measured by the motion tracking system 201 (e.g., SYNCHRONY® respiratory tracking system). By measuring the patient breathing cycle using sensor system 202 may be used as a quality assurance tool for the motion tracking system 201.

Figure 3:
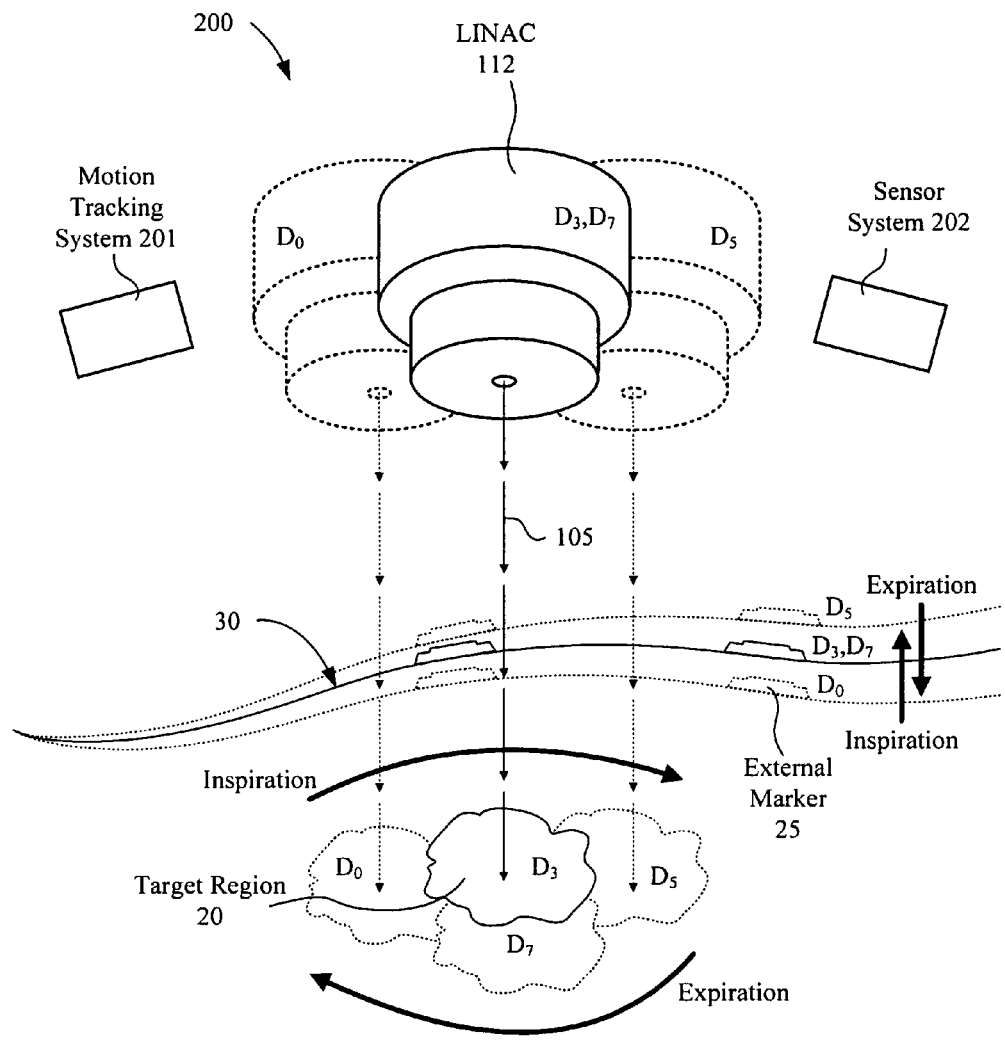
FIG. 3 illustrates a cross-sectional view of a treatment tracking environment.

FIG. 3 illustrates a cross-sectional view of a treatment tracking environment. The treatment tracking environment depicts corresponding movements of an internal target region 20 within a patient, a LINAC 112, and an external marker 25.

The illustrated treatment tracking environment is representative of a patient chest region, for example, or another region of a patient in which an internal organ might move during the respiratory cycle of the patient. In general, the respiratory cycle of a patient will be described in terms of an inspiration interval and an expiration interval, although other designations and/or delineations may be used to describe a respiratory cycle.

In one embodiment, the LINAC 112 moves in one or more dimensions to position and orient itself to deliver a radiation beam 105 to the target region 20. Although substantially parallel radiation beams 105 are depicted, the LINAC 112 may move around the patient in multiple dimensions to project radiation beams 105 from several different locations and angles. The LINAC 112 tracks the movement of the target region 20 as the patient breathes, for example. One or more external markers 25 are secured to the exterior 30 (e.g., surface 204) of the patient in order to monitor the patient's breathing cycle. In one embodiment, the external marker 25 may be a device such as a light source or a metal button attached to a vest worn by the patient. Alternatively, the external marker 25 may be attached to the patient's clothes or skin in another manner.

As the patient breathes, a motion tracking system 201 tracks the location of the external marker 25. For example, the tracking sensor may track upward movement of the external marker 25 during the inspiration interval and downward movement of the external marker 25 during the expiration interval. The relative position of the external marker 25 is correlated with the location of the target region 20, so that the LINAC 112 may move relative to the location of the external marker 25 and the correlated location of the target region 20. In another embodiment, other types of external or internal markers may be used instead of or in addition to the illustrated external marker 25.

As one example, the depicted target region 20 is shown four positions designated as $D_0$, $D_3$, $D_5$, and $D_7$. The first position, $D_0$, may correspond to approximately the beginning of the inspiration interval. The second position, $D_3$, may correspond to a time during the inspiration interval. The third position, $D_5$, may correspond to approximately the end of the inspiration interval and the beginning of the expiration interval. The fourth position, $D_7$, may correspond to a time during the expiration interval. As the patient breathes, the target region 20 may move along a path within the patient's body. In one embodiment, the path of the target region 20 is asymmetric in that the target region 20 travels along different paths during the inspiration and expiration intervals. In another embodiment, the path of the target region 20 is at least partially non-linear. The path of the target region 20 may be influenced by the size and shape of the target region 20, organs and tissues surrounding the target region 20, the depth or shallowness of the patient's breathing, and so forth.

Similarly, the external marker 25 is shown in a first position, Do, a second position, $D_3$, a third position, $D_5$, and a fourth position, $D_7$, which correspond to the positions of the target region 20. By correlating the positions of the external marker 25 to the target region 20, the position of the target region 20 may be derived from the position of the external marker 25 even though the external marker 25 may travel in a direction or along a path that is substantially different from the path and direction of the target region 20. The LINAC 112 is also shown in a first position, $D_0$, a second position, $D_3$, a third position, $D_5$, and a fourth position, $D_7$, which also correspond to the positions of the target region 20. In this way, the movements of the LINAC 112 may be substantially synchronized to the movements of the target region 20 as the position of the target region 20 is correlated to the sensed position of the external marker 25.

By tracking the position of the target region 20 during treatment delivery and comparing the absorbed dose to the planned dose, the treatment delivery system 200 may determine if the planned dose is administered to the target region 20 or if excessive doses are administered to surrounding tissue or critical structures. Tracking the position of the target object 20 using motion tracking system 201 may be performed in a number of ways. Some exemplary tracking technologies include fiducial tracking, soft-tissue tracking, and skeletal structure tracking, which are known in the art; accordingly, a detailed discussion is not provided.

In another embodiment, the treatment delivery system 200 may tally the absorbed dose during a single session as each radiation beam is administered. In this way, the treatment delivery system may potentially adjust the current treatment session in response to a determination that more or less radiation should be delivered to the target region 20 or surrounding tissue or structures. For example, the treatment delivery system may adjust the time duration of the radiation beam in subsequent treatment positions to optimize the absorbed dose relative to the treatment plan, given the treatment conditions of the current session. Alternatively, the treatment delivery system may iteratively adjust the intensity of the radiation beam in current or subsequent treatment positions to optimize the absorbed dose relative to the treatment plan.

During treatment delivery the actual absorbed dose may be differ from the planned dose. The difference may be an underdosage or an overdosage of radiation. For underdosage, the area inside the target region 20 received less radiation than the planned radiation dose. For overdosage, the area outside the target region 20 receives more than the planned radiation dose. In one embodiment, treatment delivery software or other system components facilitate determining the actual dose isocontours, based on one or more treatment delivery conditions. Treatment delivery conditions refer generally to factors that may influence the delivery of the radiation treatment, and are divided into two categories: delivery parameters and external factors. Delivery parameters are factors controlled by or subject to the treatment delivery system. Exemplary delivery parameters that influence the actual dosage absorbed at a target region 20 may include, but are not limited to, calibration tolerances, beam positions, beam orientations, beam shapes, beam intensity, beam status, attenuation of absorption of intervening tissues and structures, and so forth. External factors, or other factors, are external to the treatment delivery system. Exemplary external factors that may influence the actual dosage absorbed at a target region 20 include, but are not limited to, ambient temperature, humidity, air pressure, and so forth.

A treatment delivery process may include calculating a dose difference using the actual absorbed dose and the planned dose, and modifying a current treatment session using the dose difference. More specifically, the planned dose from the treatment plan is delivered to the treatment delivery system, which attempts to deliver the planned dose. However, the absorbed dose may be different from the planned dose due to circumstances during the treatment delivery that might be different from the assumptions used to generate the treatment plan, such as the target depth 205 of the target region 20. Therefore, the treatment delivery system calculates the absorbed dose based on the actual absorbed dose. For example, the treatment plan may assume that the target region 20 is located at a particular depth during radiation treatment, but the actual target depth of the target region 20 during radiation treatment may be different from the planned position. The difference in depths may be caused by motion of the surrounding tissue with respect to the target region during treatment. Alternatively, the difference in target depths may occur between treatment planning and treatment delivery, for example, the target region 20 may have shifted, increased/decreased in side, or the like. This difference in depths may be determined by tracking the target region 20 during radiation treatment using fiducial, soft-tissue, skeletal, or another tracking technology, and by determining the actual point of entry 206 to determine the actual target depth 205 during treatment. Given the difference in depths, the absorbed dose to the target region may be more or less than the planned dose. Other factors, in addition to location, may affect the actual absorbed dose 104. For example, the absorbed dose may depend on one or more of the following: air pressure, temperature, humidity, duration that the beam is on, and so forth.

The treatment delivery system 200 uses the planned dose and the absorbed dose to generate a dose difference, which represents the difference between the planned dose and the absorbed dose. In one embodiment, the dose difference may be zero for a given beam or set of beams where the radiation that is actually delivered is the same as the radiation specified in the treatment plan. In another embodiment, the dose difference may specify areas of underdosage, overdosage, or both compared to the treatment plan. The dose difference may be used in determining the delivery parameters of one or more subsequent radiation beams in the current treatment session. In one embodiment, the comparison between the treatment plan and the actual treatment delivery may occur with each radiation beam. In another embodiment, the comparison between the treatment plan and the actual treatment delivery may result in a cumulative dose difference, taking into account any resulting adjustments to the actual radiation delivered to the target region 20 or the surrounding soft tissue and critical structures.

In one embodiment, using the dose difference to determine a delivery parameter of a subsequent radiation beam may be an operation within a process to generate and implement a treatment delivery modification. A treatment delivery modification may be generated based on a previous treatment plan or may be independently generated. More generally, the treatment delivery system 200 may generate a treatment delivery modification based on any actual delivery condition that differs from a condition assumed in the treatment plan. For example, if the treatment plan generated during the treatment planning phase uses an assumption that the beam will be on for a given duration, but since the target depth has actually increased during treatment, then the treatment delivery system may generate and implement a treatment delivery modification during the treatment delivery phase that compensates for the underdosage in subsequent radiation delivery portions.

In another embodiment, the treatment delivery system 200 may modify a subsequent treatment session rather than the current treatment session. This treatment delivery process includes calculating a dose difference using the absorbed dose of a current session, and modifying a subsequent treatment session using the dose difference. More specifically, the planned dose from the treatment plan is delivered to the treatment delivery system 200, which attempts to deliver the planned dose. However, the absorbed dose may be different from the planned dose due to circumstances during the treatment delivery that might be different from the assumptions used to generate the treatment plan, such as the actual target depth 205 during treatment. Therefore, the treatment delivery system calculates the absorbed dose based on the actual treatment conditions.

The treatment delivery system 200 uses the planned dose and the absorbed dose to generate a dose difference, which represents the difference between the planned dose and the absorbed dose. The dose difference may be used in determining the delivery parameters of one or more subsequent treatment sessions. In one embodiment, the dose difference may be used to modify a treatment plan of a subsequent treatment session. In another embodiment, the dose difference may be used to modify a treatment delivery of a subsequent treatment session, rather than the subsequent treatment planning. In another embodiment, the dose difference may be used to modify both a current treatment session and a subsequent treatment session. In another embodiment, the treatment delivery system 200 may present real-time feedback to an operator who may authorize modifications to the current treatment session or to a subsequent treatment session.

Figure 4:
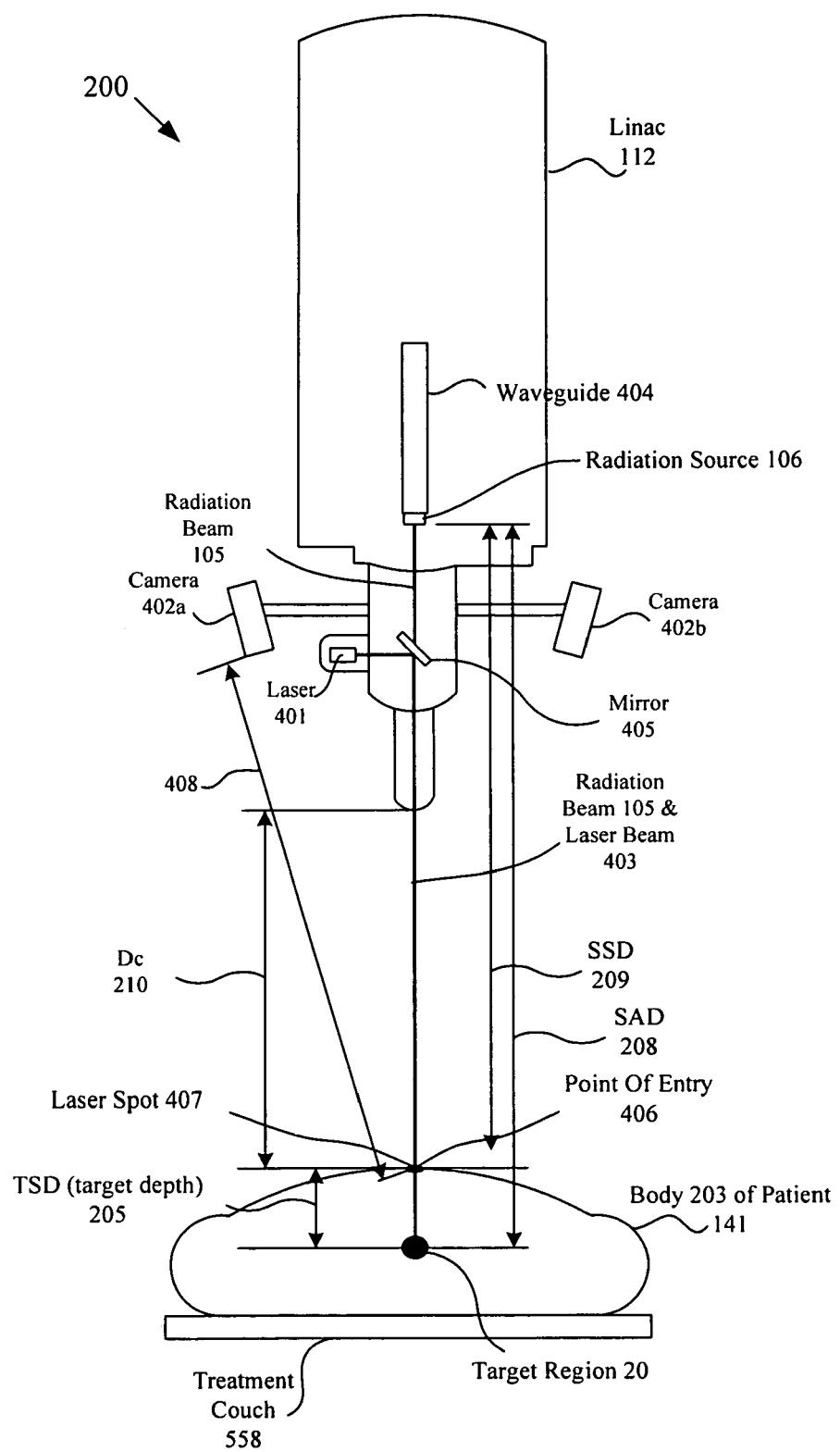
FIG. 4 is an illustration of one embodiment of a treatment delivery system including a laser and a stereo-pair of optical cameras.

FIG. 4 is an illustration of one embodiment of a treatment delivery system 200 including a laser 401 and a stereo-pair of optical cameras 402*a* and 402*b*. The cameras 402*a* and 402*b* are configured to image a surface of the body 203 to which the radiation beam 105 is directed to determine the actual point of entry 406 of the radiation beam 105 into the body 203. Treatment delivery system 200 includes LINAC 112, which includes radiation source 106, waveguide 404, and mirror 405. In LINAC 112, electrons from an electron gun at a negative potential are accelerated to the target (e.g., radiation source), which is held at a positive potential relative to the electron gun (e.g., at a system ground potential). The electrons are accelerated through a waveguide accelerator structure 404 as an electron beam that strikes an x-ray target (e.g., radiation source 106) to generate x-rays (e.g., radiation beam 105). The radiation beam 105 is directed towards target region 20, located within the body 203 of a patient 141 on a treatment couch 558. Additional details regarding the LINAC 112 are known in the art and have not been illustrated or described so as to not obscure the embodiments described herein. The embodiments described herein are not limited to robotic-based radiation treatment system, but may also include other radiation treatment systems, such as gantry-based radiation treatment systems.

Laser 401 is coupled to the LINAC 112 to provide a laser beam 403 that is coincident with the radiation beam 105. In one embodiment, the laser 401 is located in a housing that is mounted to one side of a collimator (e.g., primary collimator). Alternatively, the housing of the laser 401 may be mounted in other locations. The laser 401 generates a laser beam that is initially nominally perpendicular to the radiation beam 105. The LINAC 112 includes a mirror, mirror 405, in the path of the radiation beam 105 within the collimator. The mirror 405 is configured to allow the radiation beam 105 to pass through the mirror 405, and to reflect the laser beam (e.g., 90 degrees) to generate the laser beam 403 that is coincident and parallel to the radiation beam 105. Alternatively, the laser beam 403 may be generated and directed to the point of entry 406 on the body 203 using other configurations.

Since the laser beam 403 and radiation beam 105 are coincident with each other, the actual point of entry 406 may be determined and monitored using the laser beam 403. The laser beam 403 may generate a laser spot 407 on the surface of the body 203. The laser spot 407 may represent the place of incidence of the laser beam 403 that is coincident with the radiation beam 105. The laser spot 407 may represent the actual point of entry 406 of the radiation beam 105. One or more cameras (e.g., 402*a* and/or 402*b*) may be used to image the laser spot on the body. A processing device of the treatment delivery system 200 determines the actual point of entry 406 based on the laser spot 207, imaged by the one or more cameras.

Stereo-pair of optical cameras 402a and 402b (e.g., video cameras) are positioned to have a clear view of the actual point of entry 406 of the radiation beam 105 (e.g., indicated by laser spot 407). Using the stereo imaging geometry, and the geometrical relationship between the radiation source 106 of the radiation beam 105, and the positions of the cameras 402a and 202b, the SSD 209 may be determined. For example, the distance 408 between the cameras 402a and 402b and the point of entry 406 can be determined. Using the known geometrical relationship between the radiation source and the cameras 402a and 402b, the SSD 209 may be computed. In another embodiment, one camera 402a may be used in conjunction with the laser 401 to measure the distance between the laser spot 406 and the camera 402a. This distance, distance 408 may be used to determine the SSD 209.

Similar to how SSD 209 is computed, the distance Dc 210 may also be computed. Using the stereo imaging geometry to determine the distance 408, and the geometrical relationship between the cameras 402a and 402b and the LINAC 112 (e.g., surface of the LINAC head), the distance Dc 210 may be determined. In another embodiment, one camera 402a (or 402b) may be used with the laser 401 to determine the distance 408. Using the known geometries of the camera and the LINAC 112, the distance Dc 210 may be determined.

In one embodiment, the cameras 402a and 402b are coupled to the LINAC 112 with known geometrical relationships to the LINAC 112. For example, in one embodiment, the cameras 402a and 402b are mounted to the primary collimator using mounting devices. Alternatively, the cameras 402a and 402b are mounted to the head or body of the LINAC. It should be noted that the cameras 402a and 402b should be mounted so that they have a clear view of the actual point of entry 406 of the radiation beam 105. In another embodiment, the cameras may also be mounted to other objects within the treatment room.

In one embodiment, the sensor system 202 includes laser 401 and stereo-pair of optical cameras 402a and 402b of FIG. 4. In another embodiment, the sensor system may include a laser 401 and one optical camera 402a (or 402b). In another embodiment, the sensor system 202 includes a stereo-pair of cameras, and no laser. Alternatively, sensor system 202 may include other systems for measuring the distance through the air to the surface of the body 203, such as a sonar device that provides sound waves to determine the distance or a radar device that provides electromagnetic waves to determine the distance.

In one embodiment, the LINAC 112, laser 401, cameras 402a and 402b, and the motion tracking system 201 are all coupled to a processing device (not illustrated in FIG. 4). The processing device is configured to determine the distances (e.g., target depth 205, SSD 208, Dc 210, and distance 408) using the actual point of entry of the radiation beam 105, as described below.

After determining the point of entry 406, as describe in the embodiments above, the point of entry 406 may be used to determine either the distance Dc 210 or the target depth 205 (TSD).

In one embodiment, the distance Dc 210 may be used to avoid collisions between the housing of the radiation source (e.g., LINAC 112) and the body 203. As described above, in one embodiment, the distance Dc 210 may be computed using the known geometries of the LINAC 112 and the distance 408. Alternatively, the distance Dc 210 may be computed using the determined SSD 209 and the known geometries of the LINAC 112. In one embodiment, the radiation source 106 is a known distance from the point of the LINAC head at which the radiation beam 105 exits the housing of LINAC 112. Subtracting this dimension from SSD 209 results in the distance Dc 210. Alternatively, this dimension may be used in conjunction with the distance 408 to determine distance Dc 210.

Once the distance Dc 210 has been determined, the distance Dc 210 may be used by treatment delivery system to halt or slow the motion of the LINAC 112 to avoid a collision between the LINAC 112 and any other object in the treatment room, such as a patient. Alternatively, the treatment delivery system may use the determined distance Dc 210 to move the treatment couch and patient to avoid a collision with the LINAC 112. In another embodiment, the operation of measuring the distance Dc 210 to avoid collisions with the LINAC 112 may be implemented as a redundancy check against other collision avoidance systems known in the art that may be used with the treatment delivery system.

In one embodiment, SSD 209 may be used to determine an absorbed dose of radiation from the radiation beam 105 at the target region 20 during treatment delivery. The absorbed dose may be used to optimize radiation treatment delivery. The absorbed dose may be matched more accurately to the planned dose of the treatment plan than conventional systems that assume a static or fixed target depth in dose calculations for the treatment plan. In one embodiment, the determined SSD 209 is used in connection with the SAD 208 (e.g., which may be computed using the motion tracking system 201) to determine the target depth 205 (e.g., TSD). In effect by determining the target depth 205, the treatment delivery system 200, in one embodiment, can compensate for both the motion of the target region 20 with respect to the radiation source 106 using the motion tracking system 201 (not illustrated in FIG. 4) and the motion of the surrounding tissue relative to the target region 20 using the sensor system 202. In another embodiment, the motion tracking system 201 and the sensor system 202 may be combined into one system to compensate for both the motion of the target and the surrounding tissue.

As described above, the target region 20 and/or the surrounding tissue of the target region 20 may be moving due to respiration during treatment. In conventional systems, the treatment plan assumes a fixed target depth for the dose calculations, and accordingly, when the target depth changes during treatment due to such motions as respiration, the dose calculations may be incorrect. Unlike the conventional systems, the sensor system 202 determines the target depth 205 during treatment, allowing the actual absorbed dose absorbed at the target region 20 to match the planned dose of the treatment plan.

In one embodiment to compensate for the motion of the surrounding tissue, the time that the radiation beam 105 is directed at the target region 20 is adjusted to allow the absorbed dose at the target region 20 to match the planned dose of the treatment plan. Alternatively, other adjustments can be made to allow the absorbed dose match the planned dose, such as modifying subsequent radiation beams, sessions, or fractions of the current session.

In one embodiment to compensate for the motion of the target region, the motion of the target region 20 may be tracked during treatment delivery. The body or the radiation source 106 may be moved with respect to one another to maintain the SAD 208 despite the motion of the target region during the treatment delivery. The target region 20 may be tracked using the motion tracking system 201, using tracking technology, such as fiducial tracking, soft-tissue tracking, skeletal structure tracking, or the like.

In one embodiment, the target depth 205 may be determined by subtracting the SSD 209 from the SAD 208. Alternatively, the target depth 205 may be determined using the distance 408, the distance Dc 210, SAD 208, and the known geometries of the LINAC 112, in particular, the distance between the radiation source 106 and the LINAC head.

Figure 5A:
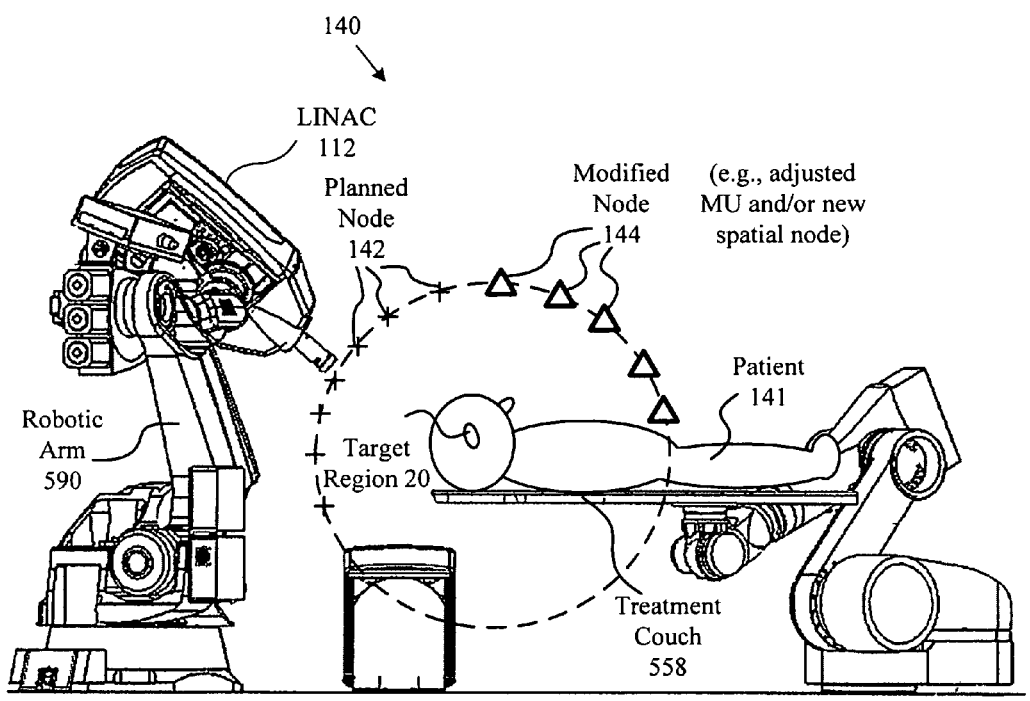
FIG. 5A illustrates a schematic diagram of one embodiment of an optimized node set.

FIG. 5A illustrates a schematic diagram of one embodiment of an optimized node set 140. In general, a node set is a collection of spatial nodes at which a radiation source 106 (e.g., of LINAC 112) may be physically located to apply radiation to a target region 20 within a patient 141. The spatial nodes (node set) and associated safe paths interconnecting these spatial nodes is called a workspace. Different types of workspaces may be created and defined during treatment planning for different patient work areas. For example, a workspace may be spherical and defined for treating a target region 20 within a patient's head. Alternatively, a workspace may have other geometries (e.g., elliptical) and defined for treating a target region 20 within another area of the patient 141. Additionally, multiple workspaces may be defined for different portions of a patient 141, each having different radius or SAD, for example, 650 mm and 800 mm.

Spatial nodes are located on the surface of workspace. The spatial nodes represent positions where the radiation source 106 of LINAC 112 may stop during treatment delivery and deliver a dose of radiation to the target region 20 within the patient 141. In one embodiment, a planning node set is defined during treatment planning. The planning node set defines one or more planned nodes 142 that may be used during treatment delivery to position the radiation source 106 of LINAC 112. Table 1 below presents exemplary values for one embodiment of a planned node set, where each planned node 142 is designated with a letter and assigned a planned MU parameter.

TABLE 1

Planned Node Set

| Node | Type | MU Parameter |
|---|---|---|
| A | PLANNED | 17.2 |
| B | PLANNED | 28.6 |
| C | PLANNED | 19.6 |
| D | PLANNED | 43.8 |
| E | PLANNED | 11.7 |
| F | PLANNED | 11.9 |
| G | PLANNED | 0 |
| H | PLANNED | 21.2 |
| I | PLANNED | 13.4 |
| J | PLANNED | 0 |
| K | PLANNED | 31.7 |
| L | PLANNED | 24.1 |

Exemplary planned nodes 142 are designated by plus ('+') symbols in FIG. 5A. Each planned node 142 designates a position and orientation of the radiation source 106 of LINAC 112, as well as an MU parameter to deliver a planned dose to the target region 20. In one embodiment, the MU parameter includes a time duration to define how long the radiation beam is on at the corresponding planned node 142 since the MU is linearly related to the time that that the radiation beam is active, as described above. In another embodiment, other parameters may be associated with the planned nodes 142.

During treatment delivery, the robotic arm 590 moves the LINAC 112 to each planned node 142. Even if a particular treatment plan does not call for delivery of a dose of radiation from a particular spatial node, the LINAC 112 still may visit that particular spatial node. In one embodiment, the LINAC 112 may deviate from the planned MU at one or more of the treatment node set and or may deviate from the planned treatment (i.e., the planned node set) in order to deliver a modified radiation dose to the target region 20. For example, a planned node 142 may be discarded and replaced by a modified node 144 at another spatial node of the workspace. In another embodiment, the modified radiation dose may correspond to a change in the amount of time the radiation beam is active at a given node or both. In other embodiments, the modified radiation dose may be implemented by varying one or more other parameters.

In the illustrated embodiment, the LINAC 112 delivers planned doses at each of a plurality of planned nodes 142. For convenience, the description herein describes the LINAC 112 as moving and applying sequential doses in a clockwise motion along the workspace (dashed circle) surrounding the target region 20 of the patient 141. In other embodiments, the LINAC 112 may move in other directions or apply doses in any order. In parallel, or substantially concurrently with the treatment delivery at the planned nodes 142, the radiation system may calculate one or more absorbed doses 104 corresponding to the radiation delivered at the planned nodes 142. The absorbed doses 104 may be the same or different from the planned doses, as described above.

If the absorbed doses (individually and/or in combination) are different from the planned doses, then the radiation system may calculate modified doses, which may be substituted for the original planned doses at subsequent modified nodes 144, which are designated by triangles in FIG. 5A. The locations of the modified nodes 144 may be the same as or different than the locations of planned nodes 142 of the treatment plan. Similarly, the radiation applied at the modified nodes 144 may be the same as or different than radiation of the planned doses defined in the treatment plan, for example, by adjusting the MU or on-time of the beam. Table 2 presents exemplary values for one embodiment of the modified node set 140, where the values for planned nodes 142 A through G are the same as in Table 1 above, and the values for planned nodes 142 H through L are replaced with modified nodes 144 generated in response to a determination that the absorbed dose 104 at planned nodes 142 A through G is not the same as the planned dose at the same nodes 142. Although MU is used in Table 2 instead of dose for convenience, other embodiments may use dose or another parameter related to dose.

TABLE 2

Modified Node Set

| Node | Type | Planned MU | Absorbed MU | Modified MU |
|---|---|---|---|---|
| A | PLANNED | 17.2 | 17.8 | |
| B | PLANNED | 28.6 | 28.2 | |
| C | PLANNED | 19.6 | 22.1 | |
| D | PLANNED | 43.8 | 40.1 | |
| E | PLANNED | 11.7 | 12.1 | |
| F | PLANNED | 11.9 | 12.6 | |
| G | PLANNED | 0 | 0 | |
| H | MODIFIED | 21.2 | | 0.8 |
| I | MODIFIED | 13.4 | | 1.8 |
| J | MODIFIED | 0 | | 3.9 |
| K | MODIFIED | 31.7 | | 6.2 |
| L | MODIFIED | 24.1 | | 2.2 |
| M | MODIFIED | NONE | N/A | 3.1 |

The example shown in Table 2 illustrates one embodiment of delivering modified radiation doses at some of the planned nodes 142 in the radiation treatment plan. In particular, the absorbed dose at each of the planned nodes 142 A through G may be determined and compared to the planned doses. In response to determining that the planned and absorbed doses are not the same, modified radiation doses may be delivered at the subsequent planned nodes 142 H-L. In the example provided, the radiation dose at the planned nodes 142 H-L are each increased by a modified dose. However, in other embodiment, the planned doses may be decreases or remain the same. Additionally, new nodes such as the modified node 144 M may be added to the radiation treatment delivery.

In another embodiment, the radiation system may implement planned nodes 142 and modified nodes 144 in any order, including alternating, depending at least in part on any dose differences between the planned doses and the absorbed doses 104 at one or more spatial nodes. Moreover, the radiation system may present modified doses in a current treatment fraction or in subsequent treatment fractions. For example, the planned doses and absorbed doses may be input into inverse planning for subsequent fractions or treatment sessions. Additionally, some embodiments having sufficient processing power may implement dose modifications in real-time during dose delivery at a node. For example, if the radiation beam is planned to be on for one time unit, the radiation system may determine during delivery of the radiation at a given node that the absorbed dose is different from the planned dose. In response to such a determination, the radiation system may dynamically modify the radiation dose and complete radiation delivery at the node according to the modified dose.

In a further embodiment, the radiation system may take into account a dynamic motion of the target in calculating the planned and absorbed doses. For example, the radiation system may consider rotation, translation, and deformation of the target over time. Rotation refers to rotation of the target about an axis with respect one of the spatial nodes. Translation refers to movement of the target in a direction with respect to one of the spatial nodes. Deformation refers to deformation of the target, e.g., stretching, twisting, etc., with respect to one of the spatial nodes. In one embodiment, the radiation system may develop two-, three-, or four-dimensional models to describe the rotation, translation, or deformation of the target. Alternatively, the radiation system may monitor the rotation, translation, and deformation of the target in real-time. Radiation doses, as well as node locations and delivery times and durations, may be modified to change the radiation dose absorbed at the target.

The illustrated optimized node set 140 is implemented via a linear accelerator (LINAC) 112 that is mounted on a robotic arm 590 (embodiments of the LINAC 112 and robotic arm 590 are described in more detail with reference to FIGS. 7 and 8). In alternative embodiments, the optimized node set 140 may be implemented using other technology such as a gantry or other radiation system.

Figure 5B:
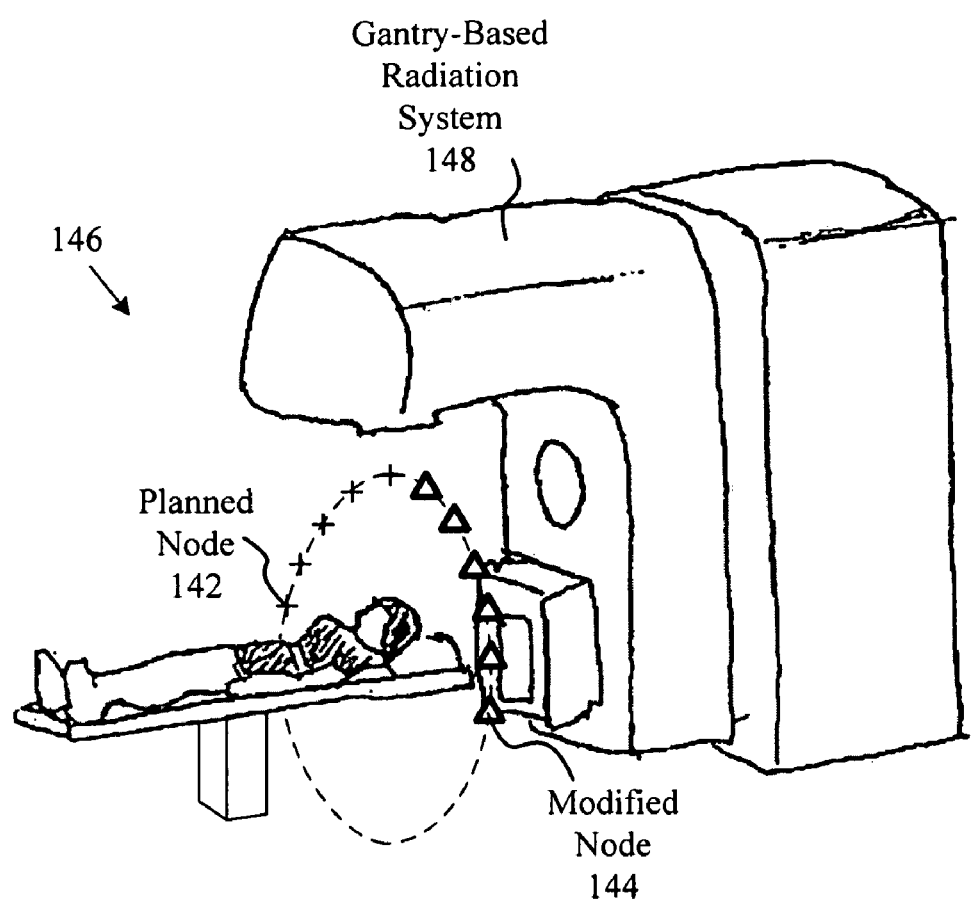
FIG. 5B illustrates a schematic diagram of another embodiment of an optimized node set.

FIG. 5B illustrates a schematic diagram of another embodiment of an optimized node set 146. In particular, the alternative optimized node set 146 may be delivered by a gantry-based radiation system or any another radiation system that is not a LINAC 112 on a robotic arm 590. Although a specific number of nodes are shown in FIGS. 5A and 5B, other implementations may employ fewer or more nodes. Furthermore, other embodiments may modify more or less nodes and may determine such modification(s) based on any number of previous nodes individually or in combination. Additionally, modified doses may be determined based on a single absorbed dose 104 or a combination of several absorbed doses 104, including absorbed doses corresponding to planned doses, modified doses, or both.

Figure 6:
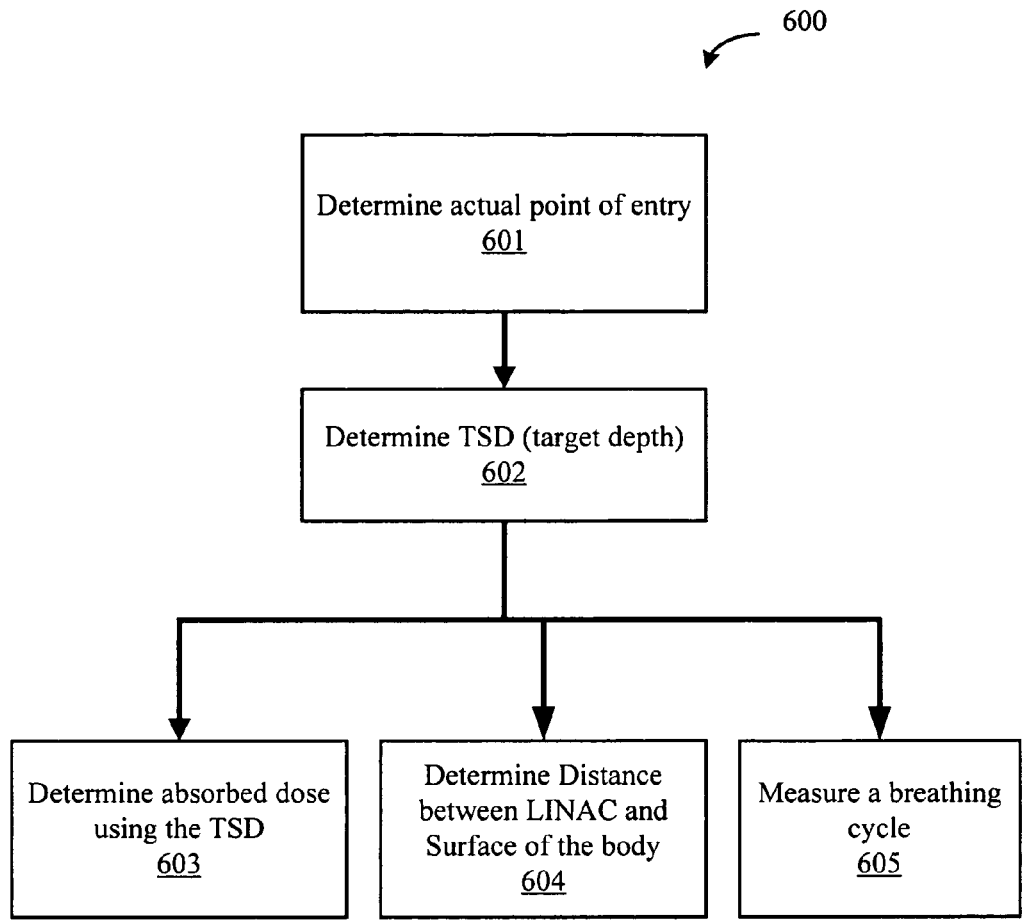
FIG. 6 illustrates a schematic flow chart of a dose comparison method.

FIG. 6 illustrates a flow chart of one embodiment of a method for determining an actual point of entry of the radiation beam and the target depth during treatment delivery. In one embodiment, method 600 may be implemented in hardware, software, and/or firmware on a treatment system, such as the treatment system 500 of FIG. 7. Although the treatment optimization method is described in terms of the treatment system 500, or certain parts of the treatment system 500, embodiments the treatment optimization method may be implemented on another system or independent of the treatment system 500.

The illustrated method begins and the treatment system 500 determines an actual point of entry (e.g., 406) of a radiation beam into a body (e.g., body 203) from a radiation source 106, operation 601. Next, using the actual point of entry, the treatment system 500 determines the TSD 205 (target depth) of the target region 20, operation 602.

Once the point of entry and the TSD have been determined, the TSD may be used to determine an absorbed dose, determine a distance Dc 210 between the LINAC 112 and the body 203 to avoid collisions, and measure of a breathing cycle of the body 203. In one embodiment of the method, the treatment system 500 may determine an absorbed dose of radiation from the radiation beam 105 at the target region 20 during treatment delivery using the TSD 205, operation 603. In another embodiment, the treatment system 500 may determine a distance Dc 210 between the housing surface of the LINAC 112 and the body 203 to avoid a collision between the housing and the body during treatment, operation 604. In another embodiment, the treatment system 500 may measure a breathing cycle of the body, operation 605. Alternatively, the treatment system 500 may perform any combination of the above operations, operations 603-605.

In another embodiment, the operation 603 of determining an absorbed dose may be used for treatment optimization method. This method may begin with the treatment planning system (e.g., 530 of FIG. 7) generating a treatment plan. In general, the treatment plan indicates certain radiation treatment parameters which are designed to deliver a particular radiation dose to a target region 20 and potentially minimize radiation exposure to surrounding tissue and structures. The treatment plan may include assumptions about the conditions of the treatment, such as the target depth for dose calculations. For example, the target depth may be based on a static CT image. The treatment delivery system (e.g., 200 of FIG. 7) then delivers a fraction of the radiation treatment according to the treatment plan. As used herein, a fraction refers to a portion of a radiation treatment plan. As described above, the actual dose absorbed via one or more radiation beams may differ from the treatment plan due to differences between the actual position of the target region 20 and the assumptions of the treatment plan (e.g., changing target depth due to motion during treatment or motion of the target region between treatment planning and treatment delivery).

The treatment delivery system (e.g., 200 of FIG. 7) subsequently evaluates the treatment delivery with respect to the treatment plan to determine if there is a difference between the actual target depth and the target depth assumed in treatment planning. The difference, if any, may result in an overdose or an underdose. If there is a difference between the actual treatment conditions and the treatment planning assumptions, then the treatment delivery system generates a treatment delivery modification based on the difference. In one embodiment, the treatment delivery modification may be described in the form of a dose difference. Alternatively, the treatment delivery modification may be described in terms of one or more treatment delivery conditions. The treatment delivery modification may be used in a current treatment session. After the treatment delivery system generates the treatment delivery modification, the treatment delivery system delivers another fraction of the radiation treatment, taking into account the treatment delivery modification. The treatment optimization method continues in this manner until all of the fractions are delivered, or until a sufficient number of fractions are delivered according to the cumulative absorbed dose and the objectives of the treatment plan.

In another embodiment the treatment optimization method may implement four-dimensional radiation treatment, including using a four-dimensional treatment plan generated using, for example, a four-dimensional CT image. The radiation system may deliver the four-dimensional treatment plan and evaluate treatment delivery with respect to the treatment plan, taking into account four-dimensional tissue movement such as rotation, translation, or deformation. Additionally, the feedback loop of the treatment optimization method may occur relatively quickly in radiation system which are capably of high processing speeds such as parallel processing. In one embodiment, the radiation system may calculate a treatment delivery modification during beam delivery at a particular node and modify the current beam delivery at the same node. Alternatively, the treatment delivery modification may be implemented at one or more subsequent nodes in the current treatment session, or at one or more nodes of a subsequent treatment session.

An alternative treatment optimization method may include operations directed to modifying a subsequent treatment session rather than a current treatment session, as illustrated and described with respect to FIG. 6. This method may also be implemented in hardware, software, and/or firmware on a treatment system, such as the treatment system.

The treatment delivery system then uses the known treatment delivery conditions to calculate and record the absorbed dose. For example, the beam intensity may be calculated relative to a calibrated intensity, given the ambient temperature and humidity, as well as a known correlation between beam intensity, temperature, and humidity. Similarly, the treatment delivery system may calculate how much radiation is actually absorbed at certain portions of the target region 20 based on the beam position, beam orientation, and actual location of the target region 20 based on the measurements of the actual point of entry and the TSD of the target region, as described herein. After calculating the absorbed dose, the treatment delivery system compares the absorbed dose to the planned dose to determine if there is a difference between the absorbed dose and the planned dose.

Figure 7:
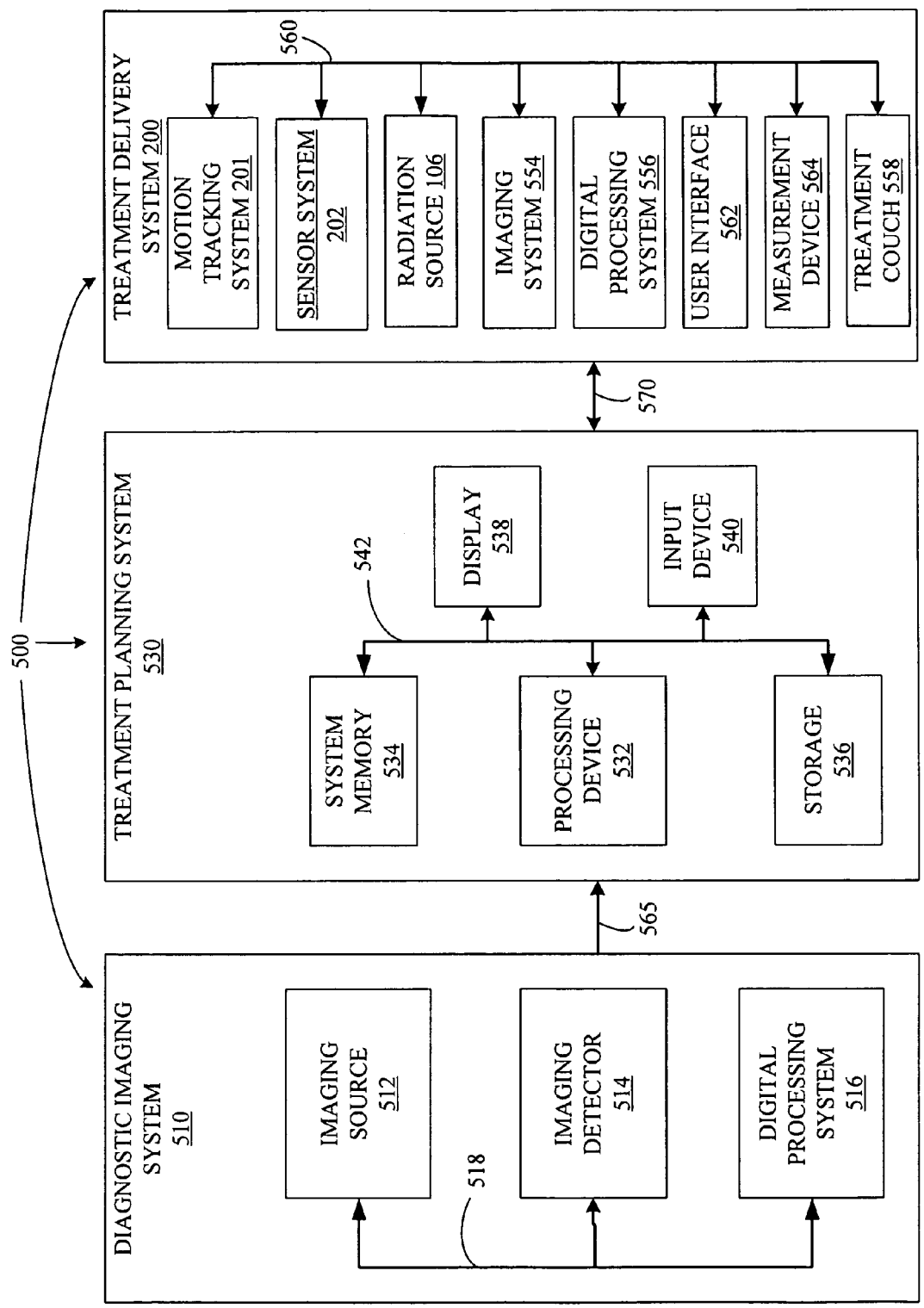
FIG. 7 illustrates one embodiment of a treatment system that may be used to perform radiation treatment in which embodiments of the present invention may be implemented.

FIG. 7 illustrates one embodiment of a treatment system 500 that may be used to perform radiation treatment in which embodiments of the present invention may be implemented. The depicted treatment system 500 includes a diagnostic imaging system 510, a treatment planning system 530, and a treatment delivery system 200. In other embodiments, the treatment system 500 may include fewer or more component systems.

The diagnostic imaging system 510 is representative of any system capable of producing medical diagnostic images of a volume of interest (VOI) in a patient, which images may be used for subsequent medical diagnosis, treatment planning, and/or treatment delivery. For example, the diagnostic imaging system 510 may be a computed tomography (CT) system, a single photon emission computed tomography (SPECT) system, a magnetic resonance imaging (MRI) system, a positron emission tomography (PET) system, a near infrared fluorescence imaging system, an ultrasound system, or another similar imaging system. For ease of discussion, any specific references herein to a particular imaging system such as a CT x-ray imaging system (or another particular system) is representative of the diagnostic imaging system 510, generally, and does not preclude other imaging modalities, unless noted otherwise.

The illustrated diagnostic imaging system 510 includes an imaging source 512, an imaging detector 514, and a digital processing system 516. The imaging source 512, imaging detector 514, and digital processing system 516 are coupled to one another via a communication channel 518 such as a bus. In one embodiment, the imaging source 512 generates an imaging beam (e.g., x-rays, ultrasonic waves, radio frequency waves, etc.) and the imaging detector 514 detects and receives the imaging beam. Alternatively, the imaging detector 514 may detect and receive a secondary imaging beam or an emission stimulated by the imaging beam from the imaging source (e.g., in an MRI or PET scan). In one embodiment, the diagnostic imaging system 510 may include two or more diagnostic imaging sources 512 and two or more corresponding imaging detectors 514. For example, two x-ray sources 512 may be disposed around a patient to be imaged, fixed at an angular separation from each other (e.g., 90 degrees, 45 degrees, etc.) and aimed through the patient toward corresponding imaging detectors 514, which may be diametrically opposed to the imaging sources 514. A single large imaging detector 514, or multiple imaging detectors 514, also may be illuminated by each x-ray imaging source 514. Alternatively, other numbers and configurations of imaging sources 512 and imaging detectors 514 may be used.

The imaging source 512 and the imaging detector 514 are coupled to the digital processing system 516 to control the imaging operations and process image data within the diagnostic imaging system 510. In one embodiment, the digital processing system 516 may communicate with the imaging source 512 and the imaging detector 514. Embodiments of the digital processing system 516 may include one or more general-purpose processors (e.g., a microprocessor), special purpose processors such as a digital signal processor (DSP), or other type of devices such as a controller or field programmable gate array (FPGA). The digital processing system 516 also may include other components (not shown) such as memory, storage devices, network adapters, and the like. In one embodiment, the digital processing system 516 generates digital diagnostic images in a standard format such as the Digital Imaging and Communications in Medicine (DICOM) format. In other embodiments, the digital processing system 516 may generate other standard or non-standard digital image formats.

Additionally, the digital processing system 516 may transmit diagnostic image files such as DICOM files to the treatment planning system 530 over a data link 560. In one embodiment, the data link 560 may be a direct link, a local area network (LAN) link, a wide area network (WAN) link such as the Internet, or another type of data link. Furthermore, the information transferred between the diagnostic imaging system 510 and the treatment planning system 530 may be either pulled or pushed across the data link 560, such as in a remote diagnosis or treatment planning configuration. For example, a user may utilize embodiments of the present invention to remotely diagnose or plan treatments despite the existence of a physical separation between the system user and the patient.

The illustrated treatment planning system 530 includes a processing device 532, a system memory device 534, an electronic data storage device 536, a display device 538, and an input device 540. The processing device 532, system memory 534, storage 536, display 538, and input device 540 may be coupled together by one or more communication channel 542 such as a bus.

The processing device 532 receives and processes image data. The processing device 532 also processes instructions and operations within the treatment planning system 530. In certain embodiments, the processing device 532 may include one or more general-purpose processors (e.g., a microprocessor), special purpose processors such as a digital signal processor (DSP), or other types of devices such as a controller or field programmable gate array (FPGA).

In particular, the processing device 532 may be configured to execute instructions for performing treatment operations discussed herein. For example, the processing device 532 may identify a non-linear path of movement of a target within a patient and develop a non-linear model of the non-linear path of movement. In another embodiment, the processing device 532 may develop the non-linear model based on a plurality of position points and a plurality of direction indicators. In another embodiment, the processing device 532 may generate a plurality of correlation models and select one of the models to derive a position of the target. Furthermore, the processing device 532 may facilitate other diagnosis, planning, and treatment operations related to the operations described herein.

In one embodiment, the system memory 534 may include random access memory (RAM) or other dynamic storage devices. As described above, the system memory 534 may be coupled to the processing device 532 by the communication channel 542. In one embodiment, the system memory 534 stores information and instructions to be executed by the processing device 532. The system memory 534 also may be used for storing temporary variables or other intermediate information during execution of instructions by the processing device 532. In another embodiment, the system memory 534 also may include a read only memory (ROM) or other static storage device for storing static information and instructions for the processing device 532.

In one embodiment, the storage 536 is representative of one or more mass storage devices (e.g., a magnetic disk drive, tape drive, optical disk drive, etc.) to store information and instructions. The storage 536 and/or the system memory 534 also may be referred to as machine readable media. In a specific embodiment, the storage 536 may store instructions to perform the modeling operations discussed herein. For example, the storage 536 may store instructions to acquire and store data points, acquire and store images, identify non-linear paths, develop linear and/or non-linear correlation models, and so forth. In another embodiment, the storage 536 may include one or more databases.

In one embodiment, the display 538 may be a cathode ray tube (CRT) display, a liquid crystal display (LCD), or another type of display device. The display 538 displays information (e.g., a two-dimensional or three-dimensional representation of the VOI) to a user. The input device 540 may include one or more user interface devices such as a keyboard, mouse, trackball, or similar device. The input device(s) 540 may also be used to communicate directional information, to select commands for the processing device 532, to control cursor movements on the display 538, and so forth.

Although one embodiment of the treatment planning system 530 is described herein, the described treatment planning system 530 is only representative of an exemplary treatment planning system 530. Other embodiments of the treatment planning system 530 may have many different configurations and architectures and may include fewer or more components. For example, other embodiments may include multiple buses, such as a peripheral bus or a dedicated cache bus. Furthermore, the treatment planning system 530 also may include Medical Image Review and Import Tool (MIRIT) to support DICOM import so that images can be fused and targets delineated on different systems and then imported into the treatment planning system 530 for planning and dose calculations. In another embodiment, the treatment planning system 530 also may include expanded image fusion capabilities that allow a user to plan treatments and view dose distributions on any one of various imaging modalities such as MRI, CT, PET, and so forth. Furthermore, the treatment planning system 530 may include one or more features of convention treatment planning systems.

In one embodiment, the treatment planning system 530 may share a database on the storage 536 with the treatment delivery system 200 so that the treatment delivery system 200 may access the database prior to or during treatment delivery. The treatment planning system 530 may be linked to treatment delivery system 200 via a data link 570, which may be a direct link, a LAN link, or a WAN link, as discussed above with respect to data link 560. Where LAN, WAN, or other distributed connections are implemented, any of components of the treatment system 500 may be in decentralized locations so that the individual systems 510, 530 and 200 may be physically remote from one other. Alternatively, some or all of the functional features of the diagnostic imaging system 510, the treatment planning system 530, or the treatment delivery system 200 may be integrated with each other within the treatment system 500.

The illustrated treatment delivery system 200 of FIG. 7 includes a motion tracking system 201, a sensor system 202, a radiation source 106 of LINAC 112, an imaging system 554, a digital processing system 556, and a treatment couch 558. The motion tracking system 201, sensor system 202, radiation source 106, imaging system 554, digital processing system 556, and treatment couch 558 may be coupled to one another via one or more communication channels 560. One example of a treatment delivery system 200 is shown and described in more detail with reference to FIG. 8.

In one embodiment, the motion tracking system 201 is configured to locate and track the motion of target region 20 during treatment, due to respiration, for example. Motion tracking system 201 also is configured to compensate for the motion of the target region 20 during treatment delivery. In one embodiment, the LINAC 112, which includes radiation source 106, may be moved to compensate for the motion of target region 20, as determined by motion tracking system 201. The LINAC 112 may move to keep the SAD 208 fixed. Alternatively, the LINAC 112 is stationary, and the motion tracking system 201 determines a different value for SAD 208. In one embodiment, the motion tracking system 201 is the SYNCHRONY® respiratory tracking system, manufactured by Accuray, Inc., Sunnyvale, Calif. Alternatively, other motion tracking systems may be used.

In one embodiment, the sensor system 202 is configured to determine the actual point of entry 206 of the radiation beam 105. In one embodiment, the sensor system 202 may include a stereo-pair of optical video cameras and a laser (illustrated in FIG. 4). In another embodiment, the sensor system 202 includes a single camera and a laser to determine and monitor the actual point of entry 206. In another embodiment, the sensor system 202 includes only a pair of stereo cameras to determine and monitor the actual point of entry 206. Alternatively, the sensor system 202 may include other systems for measuring and monitoring the actual point of entry 206 to determine the distance through the air to surface of the body, such as sonar and radar devices.

In one embodiment, the radiation source 106 is a therapeutic or surgical radiation source to administer a prescribed radiation dose to a target volume in conformance with a treatment plan. For example, the target volume may be an internal organ, a tumor, a region. As described above, reference herein to the target, target volume, target region, target area, or internal target refers to any whole or partial organ, tumor region, or other delineated volume that is the subject of a treatment plan.

In one embodiment, the imaging system 554 of the treatment delivery system 200 captures intra-treatment images of a patient volume, including the target volume, for registration or correlation with the diagnostic images described above in order to position the patient with respect to the radiation source. Similar to the diagnostic imaging system 510, the imaging system 554 of the treatment delivery system 200 may include one or more sources and one or more detectors.

The treatment delivery system 200 also may include a digital processing system 556 to control the radiation source 106 (e.g., of LINAC 112), the imaging system 554, and a treatment couch 558, which is representative of any patient support device. The digital processing system 556 may include one or more general-purpose processors (e.g., a microprocessor), special purpose processors such as a digital signal processor (DSP), or other devices such as a controller or field programmable gate array (FPGA). Additionally, the digital processing system 556 may include other components (not shown) such as memory, storage devices, network adapters, and the like.

The illustrated treatment delivery system 200 also includes a user interface 562 and a measurement device 564. In one embodiment, the user interface 562 allows a user to interface with the treatment delivery system 200. In particular, the user interface 562 may include input and output devices such as a keyboard, a display screen, and so forth. In one embodiment, the radiation treatment displays 10 of FIGS. 1 through 3 are incorporated into the user interface 562. The measurement device 564 may be one or more devices that measure external factors such as the external factors described above, which may influence the radiation that is actually absorbed at the target region 20. Some exemplary measurement devices include a thermometer to measure ambient temperature, a hygrometer to measure humidity, a barometer to measure air pressure, or any other type of measurement device to measure an external factor.

Figure 8:
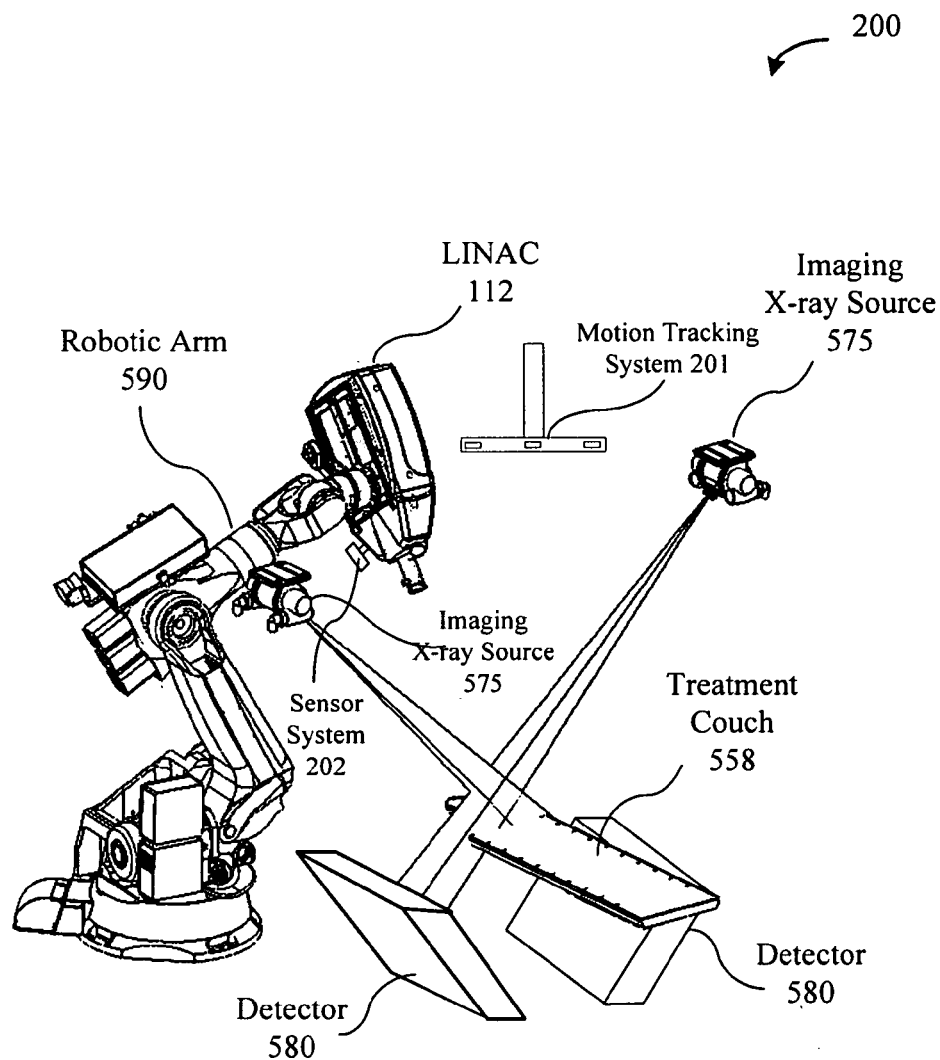
FIG. 8 is a schematic block diagram illustrating one embodiment of a t delivery system.

FIG. 8 is a schematic block diagram illustrating one embodiment of a treatment delivery system 200. The depicted treatment delivery system 200 includes a radiation source 106, in the form of a linear accelerator (LINAC), motion tracking system 201, sensor system 202, and a treatment couch 558, as described above. The treatment delivery system 200 also includes multiple imaging x-ray sources 575 and detectors 580. The two x-ray sources 575 may be nominally aligned to project imaging x-ray beams through a patient from at least two different angular positions (e.g., separated by 90 degrees, 45 degrees, etc.) and aimed through the patient on the treatment couch 558 toward the corresponding detectors 580. In another embodiment, a single large imager may be used to be illuminated by each x-ray imaging source 575. Alternatively, other quantities and configurations of imaging sources 575 and detectors 580 may be used. In one embodiment, the treatment delivery system 200 may be an image-guided, robotic-based radiation treatment system (e.g., for performing radiosurgery) such as the CyberKnifeg® system developed by Accuray Incorporated of California.

In the illustrated embodiment, the LINAC 112 is mounted on a robotic arm 590. The robotic arm 590 may have multiple (e.g., 5 or more) degrees of freedom in order to properly position the LINAC 112 to irradiate a target such as a pathological anatomy with a beam delivered from many angles in an operating volume around the patient. The treatment implemented with the treatment delivery system 200 may involve beam paths with a single isocenter (point of convergence), multiple isocenters, or without any specific isocenters (i.e., the beams need only intersect with the pathological target volume and do not necessarily converge on a single point, or isocenter, within the target). Furthermore, the treatment may be delivered in either a single session (mono-fraction) or in a small number of sessions (hypo-fractionation) as determined during treatment planning. In one embodiment, the treatment delivery system 200 delivers radiation beams according to the treatment plan without fixing the patient to a rigid, external frame to register the intra-operative position of the target volume with the position of the target volume during the pre-operative treatment planning phase.

As described above, the digital processing system 556 may implement algorithms to register images obtained from the imaging system 554 with pre-operative treatment planning images obtained from the diagnostic imaging system 510 in order to align the patient on the treatment couch 558 within the treatment delivery system 200. Additionally, these images may be used to precisely position the radiation source 106 of LINAC 112 with respect to the target volume or target.

In another embodiment, the motion tracking system 201 may be used to position the radiation source 106 of LINAC 112 with respect to the target region 20. As described above, the motion tracking system 201 is configured to track and compensate for the motion of the target region 20.

In one embodiment, the treatment couch 558 may be coupled to second robotic arm (not shown) having multiple degrees of freedom. For example, the second arm may have five rotational degrees of freedom and one substantially vertical, linear degree of freedom. Alternatively, the second arm may have six rotational degrees of freedom and one substantially vertical, linear degree of freedom. In another embodiment, the second arm may have at least four rotational degrees of freedom. Additionally, the second arm may be vertically mounted to a column or wall, or horizontally mounted to pedestal, floor, or ceiling. Alternatively, the treatment couch 558 may be a component of another mechanism, such as the AXUMS® treatment couch developed by Accuray Incorporated of California. In another embodiment, the treatment couch 558 may be another type of treatment table, including a conventional treatment table.

Although one exemplary treatment delivery system 200 is described above, the treatment delivery system 200 may be another type of treatment delivery system. For example, the treatment delivery system 200 may be a gantry based (isocentric) intensity modulated radiotherapy (IMRT) system, in which a radiation source 106 (e.g., a LINAC) is mounted on the gantry in such a way that it rotates in a plane corresponding to an axial slice of the patient. Radiation may be delivered from several positions on the circular plane of rotation. In another embodiment, the treatment delivery system 200 may be a stereotactic frame system such as the GarnmaKnife®, available from Elekta of Sweden.

Figure 9:
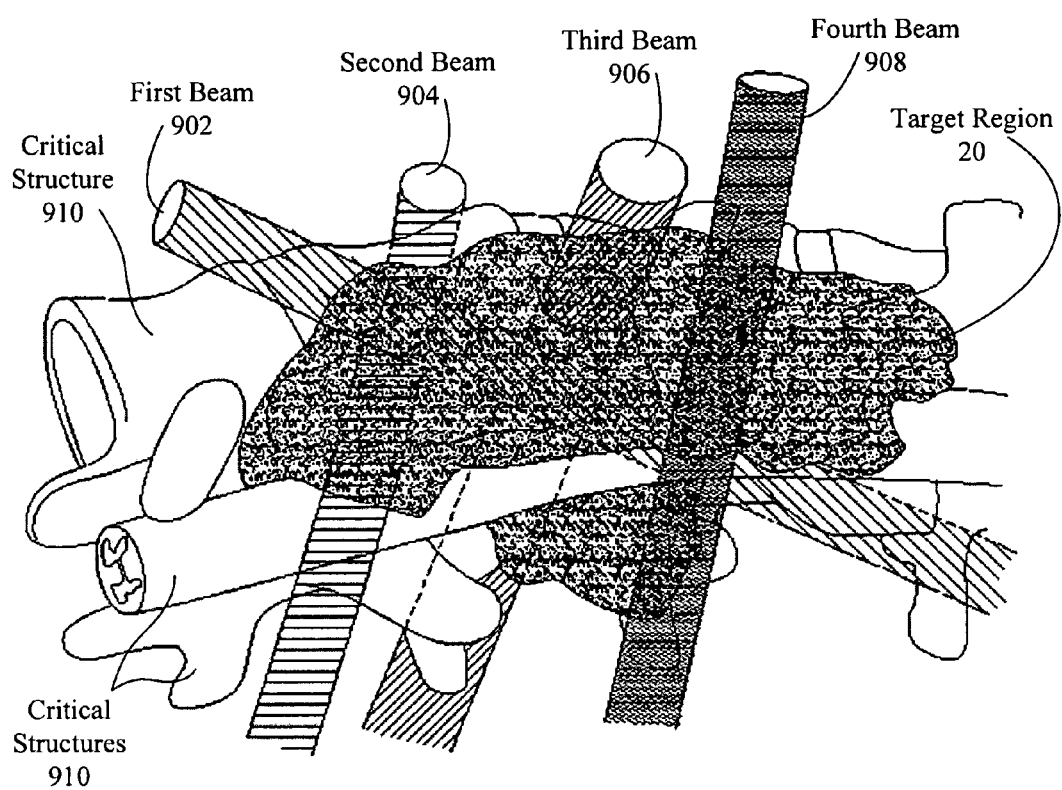
FIG. 9 illustrates a three-dimensional perspective view of a radiation treatment process.

FIG. 9 illustrates a three-dimensional perspective view of a radiation treatment process. In particular, FIG. 9 depicts several radiation beams directed at a target 20. In one embodiment, the target 20 may be representative of an internal organ, a region within a patient, a pathological anatomy such as a tumor or lesion, or another type of object or area of a patient. The target 20 also may be referred to herein as a target region, a target volume, and so forth, but each of these references is understood to refer generally to the target 20, unless indicated otherwise.

The illustrated radiation treatment process includes a first radiation beam 902, a second radiation beam 904, a third radiation beam 906, and a fourth radiation beam 908. Although four radiation beams are shown, other embodiments may include fewer or more radiation beams. For convenience, reference to one radiation beam is representative of all of the radiation beams, unless indicated otherwise. Additionally, the treatment sequence for application of the radiation beams may be independent of their respective ordinal designations.

In one embodiment, the four radiation beams are representative of beam delivery based on conformal planning, in which the radiation beams pass through or terminate at various points within target region 20. In conformal planning, some radiation beams may or may not intersect or converge at a common point in three-dimensional space. The radiation beams may be non-isocentric in that they do not necessarily converge on a single point, or isocenter. However, the radiation beams may wholly or partially intersect at the target 20 with one or more other radiation beams.

In another embodiment, the intensity of each radiation beam may be determined by a beam weight that may be set by an operator or by treatment planning software. The individual beam weights may depend, at least in part, on the total prescribed radiation dose to be delivered to target 20, as well as the cumulative radiation dose delivered by some or all of the radiation beams. For example, if a total prescribed dose of 3500 cGy is set for the target 20, the treatment planning software may automatically predetermine the beam weights for each radiation beam in order to balance conformality and homogeneity to achieve that prescribed dose.

In the depicted embodiment, the various radiation beams are directed at the target region 20 so that the radiation beams do not intersect with the critical structures 910. In another embodiment, the radiation beams may deliver radiation treatment to the target region 20 by sweeping across the target region 20, as described above. The beam sweeping radiation treatment may be effectuated or facilitated by the relative movement between the target region 20 and the beam paths of the individual radiation beams.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of a beam(s) and "target" may refer to a non-anatomical object or area.

Embodiments of the present invention include various operations, which are described herein. These operations may be performed by hardware components, software, firmware, or a combination thereof. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

The digital processing device(s) described herein may include one or more general-purpose processing devices such as a microprocessor or central processing unit, a controller, or the like. Alternatively, the digital processing device may include one or more special-purpose processing devices such as a digital signal processor (DSP), an application specific integrated circuit (ASIC), a field programmable gate array (FPGA), or the like. In an alternative embodiment, for example, the digital processing device may be a network processor having multiple processors including a core unit and multiple microengines. Additionally, the digital processing device may include any combination of general-purpose processing device(s) and special-purpose processing device(s).

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
   determining an actual point of entry of a radiation beam into a body from a radiation source; and
   determining a target-to-surface distance (TSD) between a target region in the body and the actual point of entry, wherein determining the TSD comprises:
      determining a distance from the actual point of entry and the radiation source;
      determining a source-axis distance (SAD) between the radiation source and the target region; and subtracting the distance from the SAD to determine the TSD.

2. The method of claim 1, further comprising determining an absorbed dose of radiation from the radiation beam at the target region during treatment delivery using the TSD.

3. The method of claim 1, further comprising:
compensating for motion of the target region with respect to the radiation source; and
compensating for motion of surrounding tissue relative to the target region.

4. The method of claim 3, wherein compensating for the motion of the surrounding tissue comprises adjusting a time that the radiation beam is directed at the target region to allow the absorbed dose at the target region to match a planned dose of a treatment plan.

5. The method of claim 3, wherein the motion of the target region and the motion of the surrounding region is caused by respiration during treatment delivery.

6. The method of claim 3, wherein compensating for the motion of the target comprises:
tracking the motion of the target region during treatment delivery; and
moving at least one of the body or the radiation source with respect to one another to maintain a source-axis distance (SAD) between the radiation source and the target region despite the motion of the target region during the treatment delivery.

7. The method of claim 6, wherein tracking comprises tracking the target region using at least one of fiducial tracking, soft-tissue tracking, or skeletal structure tracking.

8. The method of claim 1, further comprising:
delivering a portion of a radiation treatment to the target region of the body based on a treatment plan, wherein the treatment plan comprises a plan dose;
determining an absorbed dose of the radiation treatment absorbed at the target region based on the determined TSD; and
modifying a subsequent portion of the radiation treatment based on a determination that the absorbed dose is different from the plan dose.

9. The method of claim 8, further comprising comparing the absorbed dose to the plan dose to identify a difference between the absorbed dose and the plan dose.

10. The method of claim 9, wherein modifying the subsequent portion of the radiation treatment comprises compensating for the difference, wherein compensating for the difference comprises at least one of:
directing the radiation beam to the target region at a current node for a longer period of time until the absorbed dose of the radiation treatment matches the plan dose of the treatment plan; or
directing an additional radiation beam to the target region at one or more different nodes until the absorbed dose of the radiation treatment matches the plan dose of the treatment plan.

11. The method of claim 9, wherein the difference is due to a change in the TSD from treatment planning to treatment delivery.

12. The method of claim 9, wherein the difference is due to a change in the TSD from movement of surrounding tissue with respect to the target region during treatment delivery.

13. The method of claim 12, wherein the movement of the surrounding tissue is due to respiration motion of the body.

14. The method of claim 8, wherein modifying the subsequent portion of the radiation treatment comprises modifying a current session of the radiation treatment.

15. The method of claim 8, wherein modifying the subsequent portion of the radiation treatment comprises modifying a subsequent session of the radiation treatment.

16. The method of claim 8, further comprising providing feedback to an operator during treatment delivery, wherein the feedback comprises the determined absorbed dose or another dose value derived from the determined absorbed dose.

17. The method of claim 8, further comprising using a four-dimensional tissue deformation model to determine the absorbed dose of the radiation treatment absorbed at the target region.

18. The method of claim 8, further comprising suspending the radiation treatment in response to a determination that the absorbed dose of the radiation treatment matches the plan dose of the treatment plan.

19. The method of claim 1, further comprising measuring a breathing cycle of the body using the actual point of entry.

20. The method of claim 19, further comprising correlating the measured breathing cycle to an additional breathing cycle measured by a motion tracking system.

21. The method of claim 1, further comprising imaging a surface of the body to determine the actual point of entry of the radiation beam into the body.

22. The method of claim 21, further comprising providing a laser beam that is coincident with the radiation beam to generate a laser spot that represents the place of incidence of the laser beam and the actual point of entry of the radiation beam.

23. A method, comprising:
determining an actual point of entry of a radiation beam into a body from a radiation source;
determining a target-to-surface distance (TSD) between a target region in the body and the actual point of entry; and
avoiding a collision of a housing of the radiation source and the body using the actual point of entry, wherein avoiding the collision comprises:
determining a first distance from the actual point of entry and the radiation source, wherein the radiation source is a second distance from the housing; and
subtracting the second distance from the first distance to determine the TSD.

24. An apparatus, comprising:
a radiation source to deliver a radiation beam to a target region of a body;
an sensor system coupled to the radiation source to determine an actual point of entry of the radiation beam into the body; and
a processing device coupled to the radiation source and the sensor system, wherein the processing device is operable to determine a target-to-surface distance (TSD) between the target region in the body and a surface of the body based on the determined actual point of entry, wherein the processing device is operable to determine a distance from the actual point of entry and the radiation source using the sensor system, to determine a source-axis distance (SAD) between the radiation source and the target region using a motion tracking system, and to subtract the distance from the SAD to determine the TSD.

25. The apparatus of claim 24, further comprising a motion tracking system coupled to the processing device, wherein the motion tracking system is operable to determine a source-axis distance (SAD) between the radiation source and the target region.

26. The apparatus of claim 25, wherein the motion tracking system is operable to compensate for motion of the target region, and wherein the motion tracking system is operable to maintain the SAD between the radiation source and the target region.

27. The apparatus of claim 25, wherein the sensor system is operable to determine a distance from the actual point of entry and the radiation source, and wherein the processing device is operable to determine the TSD based on the distance and the SAD.

28. The apparatus of claim 27, wherein the processing device is operable to determine an absorbed dose of radiation absorbed by the target region using the TSD.

29. The apparatus of claim 28, wherein the processing device is operable to turn off the radiation beam of the radiation source when the absorbed dose matches a pre-determined dose of a treatment plan.

30. The apparatus of claim 24, wherein the radiation source is operable to deliver a portion of a radiation treatment to the target region of the body based on a treatment plan, wherein the treatment plan comprises a plan dose, and wherein the processing device is operable to determine an absorbed dose of the radiation treatment absorbed at the target region and to modify a subsequent portion of the radiation treatment based on a determination that the delivery dose is different from the plan dose.

31. The apparatus of claim 30, wherein the processing device is operable to modify the subsequent portion of the radiation treatment in a current session of the radiation treatment.

32. The apparatus of claim 30, wherein the processing device is operable to modify the subsequent portion of the radiation treatment in a subsequent session of the radiation treatment.

33. The apparatus of claim 30, wherein the processing device is further configured to compare the absorbed dose to the plan dose to identify a difference between the absorbed dose and the plan dose.

34. The apparatus of claim 30, wherein the sensor system comprises a pair of stereo cameras, wherein the pair of stereo cameras is configured to image a surface of the body to which the radiation beam is directed to determine the actual point of entry of the radiation beam into the body.

35. The apparatus of claim 30, wherein the sensor system comprises:
a laser to provide a laser beam that is coincident with the radiation beam, wherein the laser beam generates a laser spot on the surface of the body that represents the place of incidence of the laser beam, and wherein the laser spot represents the actual point of entry; and
a video camera to image the laser spot on the body, and wherein the processing device is operable to determine the actual point of entry based on the laser spot imaged by the video camera.

36. The apparatus of claim 30, wherein the sensor system comprises:
a laser to provide a laser beam that is coincident with the radiation beam, wherein the laser beam generates a laser spot on the surface of the body that represents the place of incidence of the laser beam, and wherein the laser spot represents the actual point of entry; and
a pair of stereo video cameras to image the laser spot on the body, and wherein the processing device is operable to determine the actual point of entry based on the laser spot imaged by the pair of stereo video cameras.

37. The apparatus of claim 30, wherein the sensor system comprises a sonar device to provide sound waves to determine the actual point of entry.

38. The apparatus of claim 30, wherein the sensor system comprises a radar device to provide electromagnetic waves to determine the actual point of entry.

39. The apparatus of claim 30, further comprising a user interface coupled to the processing device, the user interface to provide real-time feedback to an operator, wherein the real-time feedback comprises the determined absorbed dose or another dose value derived from the determined absorbed dose.

40. The apparatus of claim 30, further comprising a treatment planning system coupled to the processing device, the treatment planning system to generate the treatment plan.

41. The apparatus of claim 40, further comprising a diagnostic imaging system coupled to the treatment planning system, the diagnostic imaging system to generate an image of the target region and communicate a representation of the image to the treatment planning system.

42. The apparatus of claim 30, further comprising an imaging system coupled to the digital processing device, the imaging system to determine a real-time position of the target region relative to the radiation source.

43. The apparatus of claim 42, further comprising:
a user interface coupled to the processing device;
a memory device coupled to the processing device; and
a measurement device coupled to the processing device.

44. The apparatus of claim 24, further comprising a treatment couch, wherein the processing device is further configured to move the radiation source or the treatment couch or both to produce a relative movement between the target region and the radiation source.

45. The apparatus of claim 24, wherein the radiation source comprises a linear accelerator (LINAC) mounted to a robotic arm.

46. The apparatus of claim 24, wherein the radiation source comprises a linear accelerator (LINAC) mounted to a gantry.

47. An apparatus, comprising:
a radiation source to deliver a radiation beam to a target region of a body;
means for determining an actual point of entry of a radiation beam into a body from a radiation source;
means for determining a distance from the actual point of entry and the radiation source; and
means for determining the distance from a source-axis distance (SAD) between the radiation source and the target region to determine a target-to-surface distance (TSD) between a target region in the body and a surface of the body based on the determined actual point of entry.

48. The apparatus of claim 47, further comprising means for compensating for motion of the target region and motion of the surrounding tissue relative to the target region during.

49. The apparatus of claim 47, further comprising means for delivering radiation beams to the target region whose surrounding tissue is moving with respiration during treatment delivery.

50. The apparatus of claim 47, further comprising means for determining radiation dose of the radiation beams absorbed at the target region.

51. The apparatus of claim 47, further comprising:
means for radiating the target region based on a treatment plan, the treatment plan comprising a plan dose;
means for determining an absorbed dose absorbed at the target region based on the determined TSD; and means for implementing a treatment delivery modification to supplement the treatment plan during treatment delivery based on a difference between the absorbed dose and the plan dose.

52. The apparatus of claim 51, further comprising means for modifying a radiation treatment session to compensate for the difference between the plan dose and the absorbed dose, wherein the radiation treatment session comprises a current session or a subsequent session.

* * * * *